(12) United States Patent
Thyagarajan

(10) Patent No.: US 12,207,930 B2
(45) Date of Patent: Jan. 28, 2025

(54) NON-INVASIVE TRANSCRANIAL STIMULATION SYSTEM AND METHOD USING PRE-RECORDED NEUROSTIMULATION DATA

(71) Applicant: Palo Alto Research Center Incorporated, Palo Alto, CA (US)

(72) Inventor: Krishnan Thyagarajan, Mountain View, CA (US)

(73) Assignee: Xerox Corporation, Norwalk, CT (US)

( * ) Notice: Subject to any disclaimer, the term of this patent is extended or adjusted under 35 U.S.C. 154(b) by 152 days.

(21) Appl. No.: 17/128,740

(22) Filed: Dec. 21, 2020

(65) Prior Publication Data

US 2022/0193455 A1 Jun. 23, 2022

(51) Int. Cl.
*A61B 5/246* (2021.01)
*A61B 5/00* (2006.01)
*A61N 7/00* (2006.01)

(52) U.S. Cl.
CPC ............ *A61B 5/246* (2021.01); *A61B 5/6803* (2013.01); *A61N 7/00* (2013.01); *A61B 5/4011* (2013.01);
(Continued)

(58) Field of Classification Search
CPC ..... A61B 5/246; A61B 5/6803; A61B 5/4011; A61B 2018/00988; A61B 2090/502;
(Continued)

(56) References Cited

U.S. PATENT DOCUMENTS

| | | |
|---|---|---|
| 6,663,571 B1 | 12/2003 | Njemanze |
| 6,827,926 B2 | 12/2004 | Robinson et al. |

(Continued)

FOREIGN PATENT DOCUMENTS

| | | |
|---|---|---|
| WO | 2011/109080 | 9/2011 |
| WO | 2020/047006 | 3/2020 |
| WO | 2020/049568 | 3/2020 |

OTHER PUBLICATIONS

Arzi et al., "Olfactory Perception as a Compass for Olfactory Neural Maps", Trendsd Cogn Sci, Nov. 2011, No. 15(11), pp. 537-545.

(Continued)

*Primary Examiner* — Hien N Nguyen
(74) *Attorney, Agent, or Firm* — Mueting Raasch Group

(57) ABSTRACT

An electronic memory is configured to store pre-recorded neurostimulation data comprising patterns of stimulation of a specified region of a subject's brain developed to recreate a response by one or more of a sensing organ or sensing organs, a vestibular system, and a memory of the subject. A focused ultrasound transducer arrangement is operably coupled to the electronic memory and comprises an array of ultrasound transducers. The focused ultrasound transducer arrangement is configured to deliver transcranial stimulation to the specified region of a person's brain using the pre-recorded neurostimulation data to recreate the response by one or more of the sensing organ or sensing organs, the vestibular system, and the memory of the subject. A support structure is configured for placement on or about a person's head. The support structure is configured to support at least the focused ultrasound transducer arrangement.

21 Claims, 28 Drawing Sheets

(52) U.S. Cl.
CPC ............... *A61N 2007/0026* (2013.01); *A61N 2007/0056* (2013.01)

(58) Field of Classification Search
CPC .............. A61N 7/00; A61N 2007/0026; A61N 2007/0056; A61N 2007/0078; A61N 2007/0095
See application file for complete search history.

(56) References Cited

U.S. PATENT DOCUMENTS

| | | | |
|---|---|---|---|
| 6,906,050 | B2 | 6/2005 | Robinson |
| 7,647,404 | B2 | 1/2010 | Cooper et al. |
| 8,591,392 | B2 | 11/2013 | Bentwich et al. |
| 9,042,201 | B2 | 5/2015 | Tyler et al. |
| 9,320,813 | B2 | 4/2016 | Peyman |
| 9,729,252 | B2 | 8/2017 | Tyler et al. |
| 10,022,457 | B2 | 7/2018 | Peyman |
| 10,350,410 | B2 | 7/2019 | Tass et al. |
| 10,695,574 | B2 | 6/2020 | Stocco et al. |
| 10,722,711 | B2 | 7/2020 | Tass |
| 10,983,177 | B2 * | 4/2021 | JimÉNez-MartÍNez ................... G01R 33/07 |
| 2005/0137180 | A1 | 6/2005 | Robinson et al. |
| 2005/0226810 | A1 | 10/2005 | Robinson |
| 2009/0326341 | A1 | 12/2009 | Furlan |
| 2014/0057232 | A1 * | 2/2014 | Wetmore ............... G09B 19/00 600/28 |
| 2014/0074076 | A1 * | 3/2014 | Gertner ................... A61B 6/12 606/169 |
| 2014/0194726 | A1 | 7/2014 | Mishelevich et al. |
| 2014/0271920 | A1 | 9/2014 | Stroebe |
| 2015/0182756 | A1 | 7/2015 | Peyman |
| 2016/0143541 | A1 | 5/2016 | He et al. |
| 2016/0334370 | A1 * | 11/2016 | Osterfeld ........... G01R 33/1269 |
| 2017/0127971 | A1 | 5/2017 | Invitto et al. |
| 2017/0157038 | A1 | 6/2017 | Peyman |
| 2017/0333711 | A1 | 11/2017 | Tass et al. |
| 2018/0193649 | A1 | 7/2018 | Schouenborg et al. |
| 2018/0369589 | A1 | 12/2018 | Schouenborg et al. |
| 2019/0082990 | A1 | 3/2019 | Poltorak |
| 2019/0091350 | A1 | 3/2019 | Peyman |
| 2019/0105517 | A1 | 4/2019 | Tyler |
| 2019/0134401 | A1 | 5/2019 | Schouenborg et al. |
| 2019/0247662 | A1 * | 8/2019 | Poltroak .............. A61B 5/0816 |
| 2020/0281499 | A1 | 9/2020 | Maeda et al. |

OTHER PUBLICATIONS

Lapid et al., "Neural Activity at the Human Olfactory Epithelium Reflects Olfactory Perception", Nature Neuroscience, Sep. 2011, 0 pages.

Weiss et al., "From Nose to Brain: Un-Sensed Electrical Currents Applied in the Nose Alter Activity in Deep Brain Structures", Cerebral Cortex Advanced Access, Sep. 2016, 12 pages.

* cited by examiner

NON-INVASIVE TRANSCRANIAL STIMULATION SYSTEM AND METHOD USING PRE-RECORDED NEUROSTIMULATION DATA

TECHNICAL FIELD

This disclosure relates generally to systems and methods for delivering transcranial stimulation to a specified region or regions of a person's brain using pre-recorded neurostimulation data.

BRIEF SUMMARY

Some embodiments are directed to a system comprising an electronic memory configured to store pre-recorded neurostimulation data comprising patterns of stimulation of a specified region of a subject's brain developed to recreate a response by one or more of a sensing organ or sensing organs, a vestibular system, and a memory of the subject. A focused ultrasound transducer arrangement is operably coupled to the electronic memory and comprises an array of ultrasound transducers. The focused ultrasound transducer arrangement is configured to deliver transcranial stimulation to the specified region of a person's brain using the pre-recorded neurostimulation data to recreate the response by one or more of the sensing organ or sensing organs, the vestibular system, and the memory of the subject. A support structure is configured for placement on or about a person's head. The support structure is configured to support at least the focused ultrasound transducer arrangement.

Some embodiments are directed to a method comprising situating a support structure on or about a subject's head, an array of magnetic sensors mounted to the support structure. The method also comprises selecting, from an electronic memory, pre-recorded neurostimulation data developed to recreate a response by one or more of a sensing organ or organs, a vestibular system, and a memory of a subject. The method further comprises delivering, using the array of ultrasound transducers and the pre-recorded neurostimulation data, transcranial stimulation to a specified region or regions of the subject's brain to recreate the response by one or more of the sensing organ or organs, the vestibular system, and the memory of the subject.

The above summary is not intended to describe each disclosed embodiment or every implementation of the present disclosure. The figures and the detailed description below more particularly exemplify illustrative embodiments.

BRIEF DESCRIPTION OF DRAWINGS

Throughout the specification reference is made to the appended drawings wherein.

The figures are not necessarily to scale. Like numbers used in the figures refer to like components. However, it will be understood that the use of a number to refer to a component in a given figure is not intended to limit the component in another figure labeled with the same number.

DETAILED DESCRIPTION OF ILLUSTRATIVE EMBODIMENTS

Embodiments of the disclosure are directed to systems and methods for recording neurostimulation data representative of patterns of stimulation of a specified region or regions of a subject's brain in response to exposing the subject to stimuli that stimulates one or more of a sensing organ or organs, vestibular system, and memory of the subject. The patterns of stimulation are stored in an electronic memory as pre-recorded neurostimulation data.

Embodiments of the disclosure are directed to systems and methods for delivering transcranial stimulation to a specified region or regions of a person's brain using pre-recorded neurostimulation data to recreate a sense of exposing one or more of a sensing organ or sensing organs, vestibular system, and memory of the subject to various stimuli.

Embodiments of the disclosure are directed to systems and methods for delivering transcranial stimulation to a specified region or regions of a person's brain using pre-recorded neurostimulation data to recreate a sense of exposing one or more of a sensing organ or sensing organs, vestibular system, and memory of the subject to various stimuli, and for transcranially sensing neural activity in the specified region or regions of the subject's brain caused by delivery of the transcranial stimulation and producing contemporaneous neurostimulation data developed using the transcranially sensed neural activity.

Past attempts to artificially stimulate the human sensory system and record the results of such artificial stimulation have seen limited success. For example, despite being one of the major five senses, the sense of olfaction has been difficult to artificially stimulate or record. Attempts at making an electronic nose, for example, have not yielded successful results. Developing a device that permits on-demand stimulation of one or more human senses (and in an advanced implementation, a device/method for recording and a closed-loop method for stimulating) is expected to have a range of applications in various industries such as perfumes and cosmetics, cognitive neuroscience, medical health, and as an extra dimension in entertainment. Embodiments of the disclosure address these and other market need by taking advantage of the high spatiotemporal resolution of neuromodulation possible through the skull using focused ultrasound, and the advantage of machine learning to permit customization of sensory organ (e.g., olfactory system) stimulation and recording for personalized sensory (e.g., fragrance) experiences.

Figure 1A:
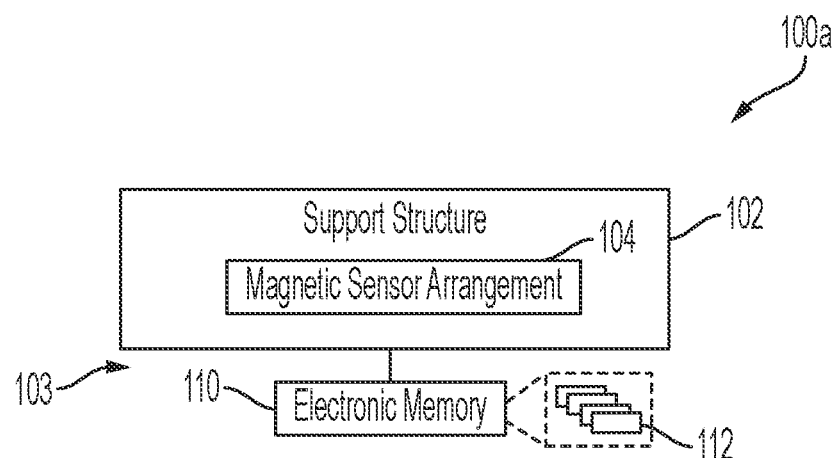
FIG. 1A illustrates a system configured to record neurostimulation information acquired using transcranial sensing of a subject's brain in accordance with various embodiments.

FIG. 1A illustrates a system 100a configured to record neurostimulation information acquired using transcranial sensing of a subject's brain in accordance with various embodiments. The system 100a includes a support structure 102 configured for placement on or about a subject's head. The support structure 102 is typically configured for placement on or about a human subject's head, but may alternatively be configured for an animal's head (e.g., a non-human primate). The system 100a includes an electronic recording apparatus 103 which includes a magnetic sensor arrangement 104 and an electronic memory 110.

The magnetic sensor arrangement 104 is mounted to, or supported by, the support structure 102. In various embodiments, the magnetic sensor arrangement 104 includes an array of magnetic sensors. In other embodiments, the magnetic sensor arrangement 104 can include a single magnetic sensor. The magnetic sensor arrangement 104 is configured for transcranial sensing of local magnetic fields emanating from a specific region of a subject's brain. The sensed local magnetic fields correspond to patterns of stimulation of the specified region of the subject's brain caused by stimulating one or more of the subject's sense organ or organs, vestibular system, and/or memory. It is understood that stimulation of a specified region of a subject's brain can refer to one or both of excitation and suppression of neural activity in the specified region of the subject's brain.

According to the embodiment shown in FIG. 1A, the electronic memory 110 is physically distinct from, and not supported by or attached to, the support structure 102. In the embodiment shown in FIG. 1A, the electronic memory 110 is operatively coupled to the magnetic sensor arrangement 104 via a wired or wireless connection. The electronic memory 110 is configured to record neurostimulation data representative of patterns of stimulation of the specified region of the subject's brain sensed by the magnetic sensor arrangement 104.

The electronic memory 110 is configured to store a multiplicity of patterns 112 of neurostimulation data associated with exposing one or more of the subject's senses to different stimuli and/or stimulating the subject's vestibular system and/or memory. The multiplicity of patterns 112 typically comprise spatiotemporal patterns of stimulation (e.g., patterns of excitation and/or suppression) recorded from the specified region of the subject's brain via the magnetic sensor arrangement 104. The spatiotemporal patterns of stimulation (also referred to as spatiotemporal neural activity patterns) include both spatial features (e.g., relative distance) and temporal features (relative timing) of neural activity that together define a particular spatiotemporal neural activity pattern.

For example, the multiplicity of patterns 112 stored in the electronic memory 110 can comprise geometric and dynamic profiles that provide a spatiotemporal representation of neural activity patterns sensed by the magnetic sensor arrangement 104. The various spatiotemporal patterns 112 stored in the memory 110 can be characterized in terms of a topographic mapping of an activity amplitude (geometric profile) and its associated temporal evolution (dynamic profile). These geometric and dynamic profiles can be used to define a spatiotemporal activity profile index to describe quantitatively each type of neural activity pattern 112 acquired by the magnetic sensor arrangement 104 and stored in the electronic memory 110.

Figure 1B:
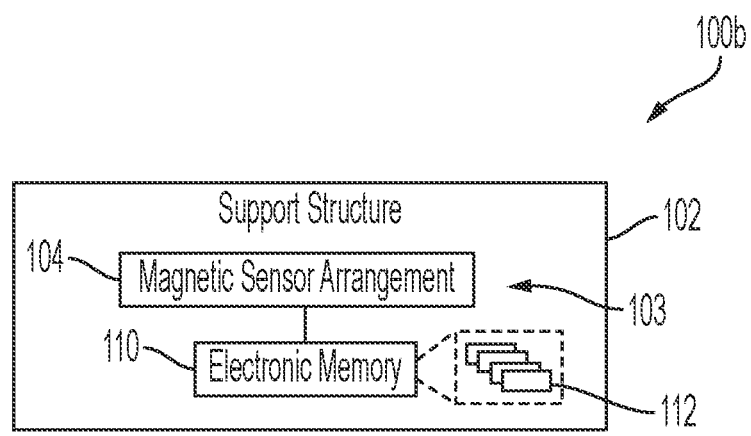
FIG. 1B illustrates a system configured to record neurostimulation information acquired using transcranial sensing of a subject's brain in accordance with various embodiments.

FIG. 1B illustrates a system 100b configured to record neurostimulation information acquired using transcranial sensing of a subject's brain in accordance with various embodiments. The system 100b includes a support structure 102 configured for placement on or about a subject's head. The system 100b includes an electronic recording apparatus 103 which includes a magnetic sensor arrangement 104 and an electronic memory 110. The magnetic sensor arrangement 104 is mounted to, or supported by, the support structure 102. The magnetic sensor arrangement 104 typically includes an array of magnetic sensors but can alternatively include a single magnetic sensor. The magnetic sensor arrangement 104 is configured for transcranial sensing of local magnetic fields emanating from a specific region of a subject's brain. As previously discussed, the sensed local magnetic fields correspond to patterns of stimulation of the specified region of the subject's brain caused by stimulating one or more of the subject's sense organ or organs, vestibular system, and/or memory.

According to the embodiment shown in FIG. 1B, the electronic memory 110 is physically attached to, or supported by, the support structure 102. The electronic memory 110 is operatively coupled to the magnetic sensor arrangement 104 typically via a wired connection, but may alternatively be coupled via a wireless connection. The electronic memory 110 is configured to record neurostimulation data representative of patterns of stimulation of the specified region of the subject's brain sensed by the magnetic sensor arrangement 104. The electronic memory 110 is configured to store a multiplicity of patterns 112 of neurostimulation data associated with exposing one or more of the subject's senses to different stimuli and/or stimulating the subject's vestibular system and/or memory.

Figure 1C:
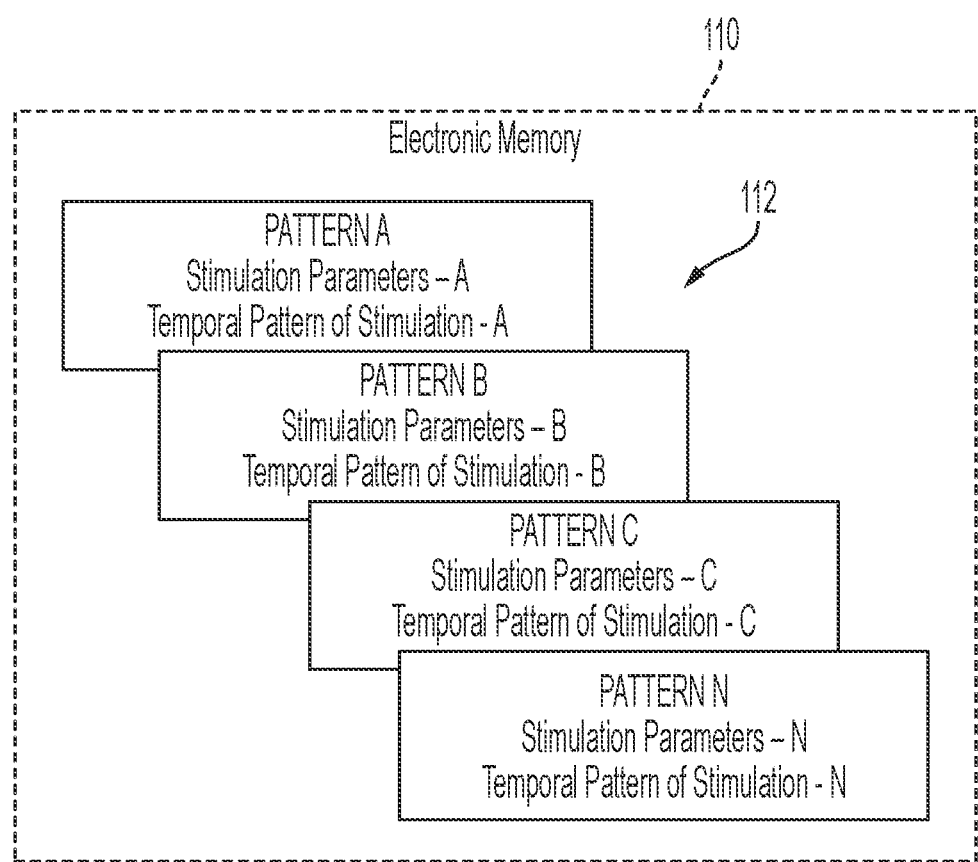
FIG. 1C illustrates representative architecture of the electronic memory shown in FIGS. 1A and 1B in accordance with various embodiments.

FIG. 1C illustrates a representative architecture of the electronic memory 110 shown in FIGS. 1A and 1B in accordance with various embodiments. The electronic memory 110 includes a multiplicity of spatiotemporal patterns 112 shown as Pattern A through Pattern N. Each of the patterns 112 is associated with neural activity sensed from a specified region of a subject's brain via the magnetic sensor arrangement 104 in response to stimulating one or more of the subject's sense organ or organs, vestibular system, and/or memory to a particular stimulus or particular stimuli. Each of the patterns 112 includes stimulation parameters (e.g., a topographic mapping of neural activity amplitude) and a temporal pattern of stimulation (e.g., a temporal mapping of the neural activity).

Figure 2A:
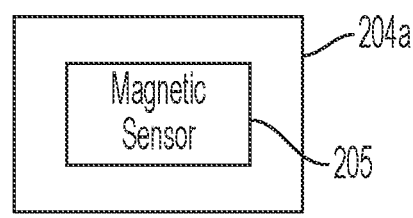
FIG. 2A illustrates a magnetic sensor arrangement in accordance with various embodiments.
Figure 2B:
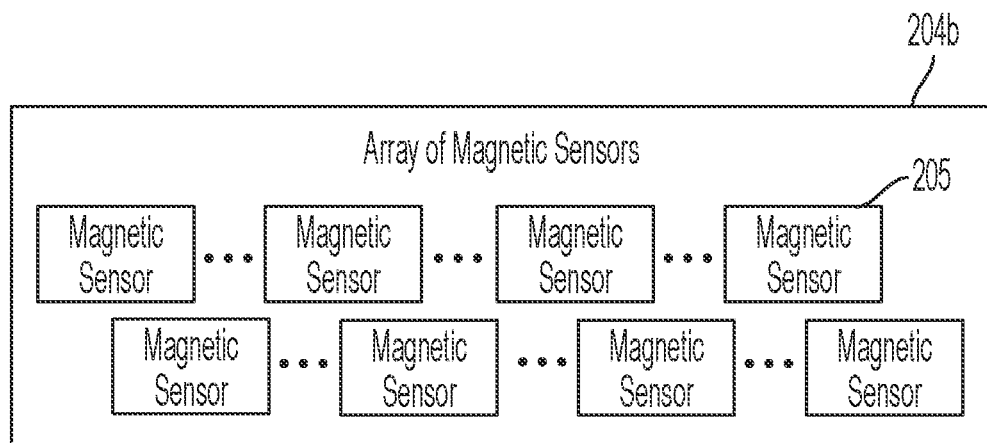
FIG. 2B illustrates a magnetic sensor arrangement in accordance with various embodiments.

FIG. 2A illustrates a magnetic sensor arrangement 204a in accordance with various embodiments. The magnetic sensor arrangement 204a shown in FIG. 2A includes a single magnetic sensor 205. In the embodiment shown in FIG. 2B, the magnetic sensor arrangement 204b includes an array of magnetic sensors 205. According to some embodiments, an individual magnetic sensor 205 can be implemented as a nitrogen-vacancy (NV) diamond magnetic sensor. In other embodiments, an individual magnetic sensor 205 can be implemented as an optically pumped magnetic (OPM) sensor. In further embodiments, an array of magnetic sensors 205, such as that shown in FIG. 2B, can include an array of NV diamond magnetic sensors, an array of OPM sensors, or a combination of NV diamond magnetic sensors and OPM sensors. Representative examples of an NV diamond magnetic sensor and an OPM sensor are described in more detail hereinbelow.

Figure 3A:
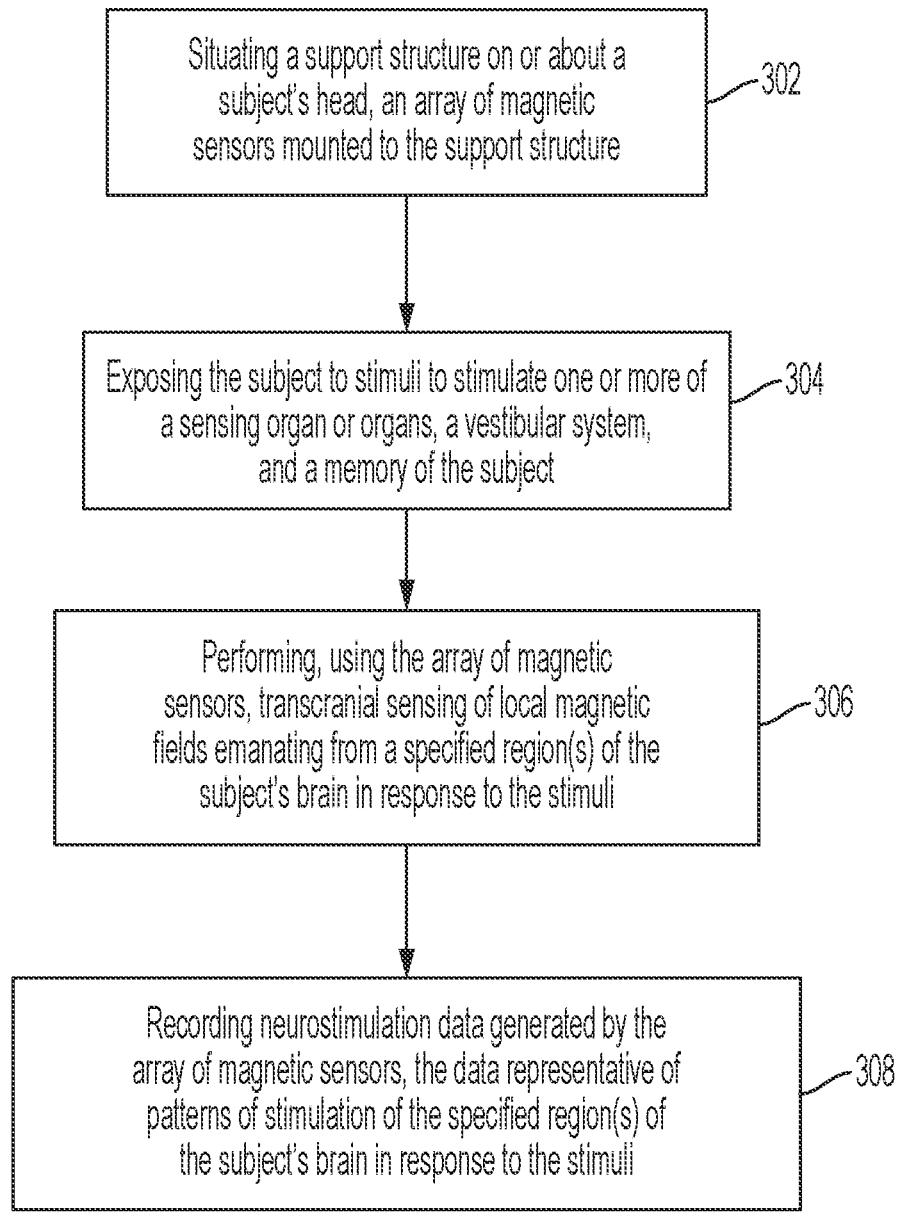
FIG. 3A illustrates a method of recording neurostimulation data generated by a magnetic sensor arrangement shown in FIGS. 1A-2B and other figures in accordance with various embodiments.

FIG. 3A illustrates a method of recording neurostimulation data generated by a magnetic sensor arrangement shown in FIGS. 1A-2B and other figures in accordance with various embodiments. Although the method shown in FIG. 3A can be implemented using a single magnetic sensor, the following discussion assumes that an array of magnetic sensors are utilized. The method shown in FIG. 3A involves situating 302 a support structure on or about a subject's head, wherein an array of magnetic sensors is mounted on the support structure. The method involves exposing 304 the subject to a stimulus or stimuli to stimulate one or more of a sensing organ or sensing organs, a vestibular system, and a memory of the subject. The method also involves performing 306, using the array of magnetic sensors, transcranial sensing of local magnetic field emanating from a specific region or regions of the subject's brain in response to the stimulus or stimuli. The method further involves recording 308 neurostimulation data generated by the array of magnetic sensors, the data representative of patterns of stimulation of the specific region or regions of the subject's brain in response to the stimulus or stimuli.

Figure 3B:
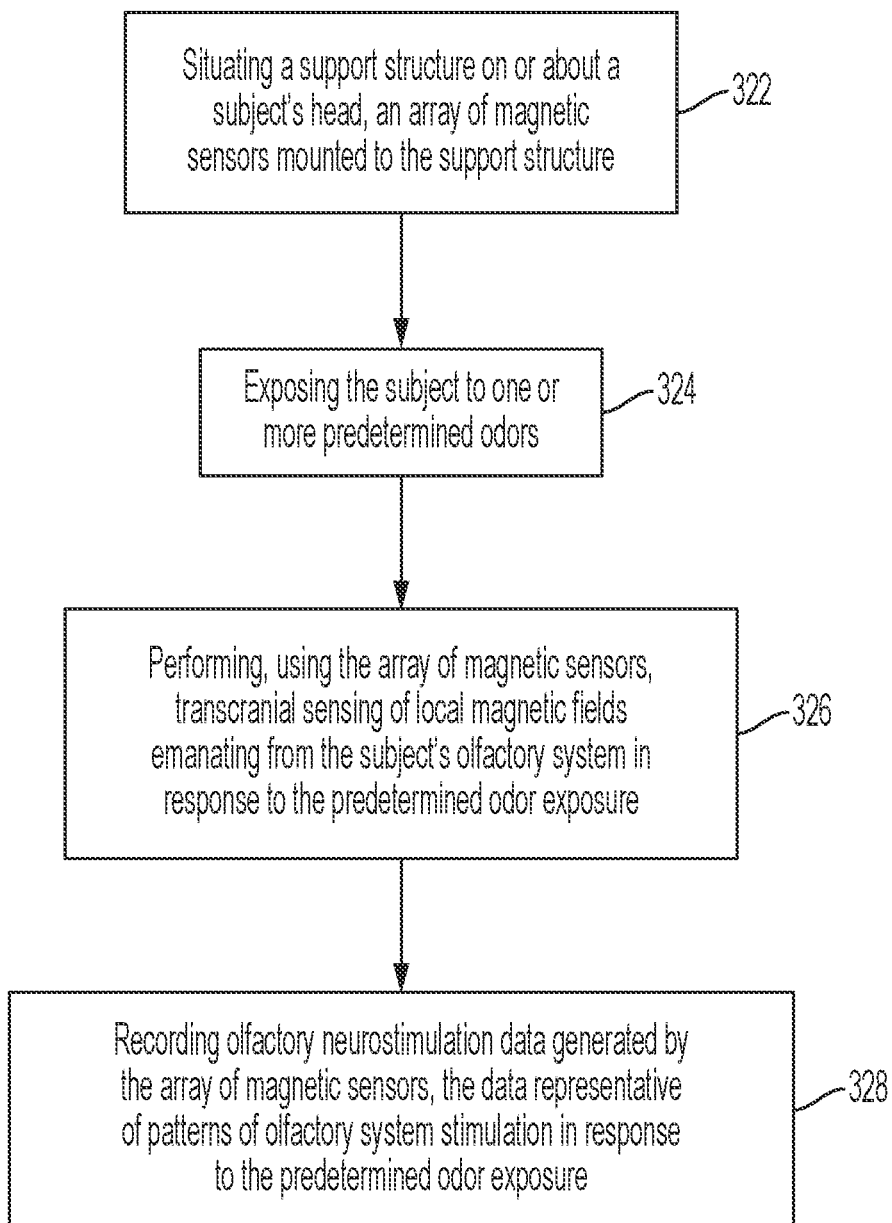
FIG. 3B illustrates a method of recording neurostimulation data generated by a magnetic sensor arrangement shown in FIGS. 1A-2B and other figures in accordance with various embodiments.

FIG. 3B illustrates a method of recording neurostimulation data generated by a magnetic sensor arrangement shown in FIGS. 1A-2B and other figures in accordance with various embodiments. The representative method shown in FIG. 3B is directed to recording neurostimulation data acquired from a subject's olfactory system. The method shown in FIG. 3B involves situating 322 a support structure on or about a subject's head, wherein an array of a magnetic sensors is mounted on the support structure. The method involves exposing 324 the subject to one or more predetermined odors. The method also involves performing 326, using the array of magnetic sensors, transcranial sensing of local magnetic fields emanating from the subject's olfactory system (e.g., olfactory cortex, piriform cortex, and/or olfactory bulb) in response to exposing the subject to the one or more predetermined odors. The method further involves recording 328 olfactory neurostimulation data generated by the array of magnetic sensors, the data representative of patterns of olfactory system stimulation in response to the predetermined odor exposure.

Figure 4A:
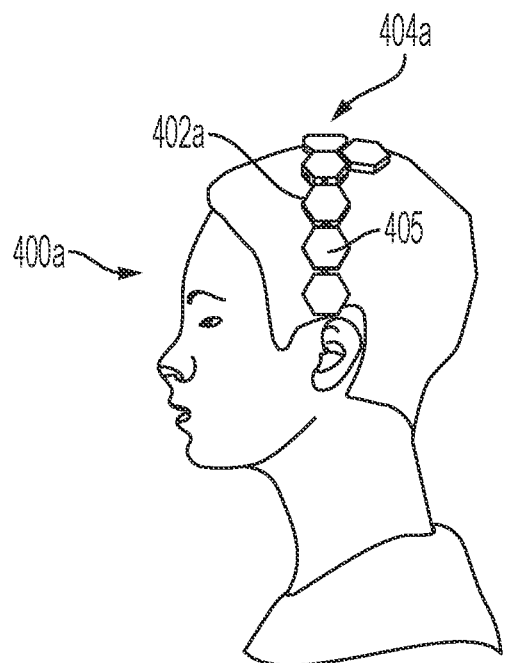
FIG. 4A illustrates a system configured to record neurostimulation information acquired using transcranial sensing of a subject's brain in accordance with various embodiments.

FIG. 4A illustrates a system 400a configured to record neurostimulation information acquired using transcranial sensing of a subject's brain in accordance with various embodiments. In the embodiment shown in FIG. 4A, the system 400a is configured to be wearable by the subject and portable, which provides for real-time operation while the subject is ambulatory. The system 400a includes a support structure 402a configured for placement on a subject's head. In the representative embodiment shown in FIG. 4A, the support structure 402a is implemented as a headband or other head-worn apparatus that extends generally from a location proximate the subject's left ear, across the left parietal ridge, over the top of the subject's head, across the right parietal ridge, and to location proximate the subject's right ear. Other configurations of the support structure 402a are contemplated.

The support structure 402a is configured to support a magnetic sensor arrangement 404a which, in the embodiment shown in FIG. 4A, includes an array of magnetic sensors 405. The magnetic sensor arrangement 404a can comprise an arrangement of interlocking magnetic sensors 405 mounted to the support structure 402a. The arrangement of interlocking magnetic sensors 405 can comprise magnetic sensors 405 configured to be mechanically interlocking, communicatively (e.g., electrically and/or optically) interlocking, or both mechanically and communicatively interlocking with one another. The magnetic sensors 405 preferably have a compact design, and can have a size less than or equal to about 2.5 cm$^2$ and/or a volume less than or equal to about 2 cm$^3$. The magnetic sensors 405 are preferably mounted to the support structure 402a such that the magnetic sensors 405 are positioned relative to a specified region or regions of the subject's brain of interest. For example, the magnetic sensors 405 can be mounted to the support structure 402a relative to specific regions of the subject's olfactory system, including the olfactory cortex and the piriform cortex.

Figure 4B:
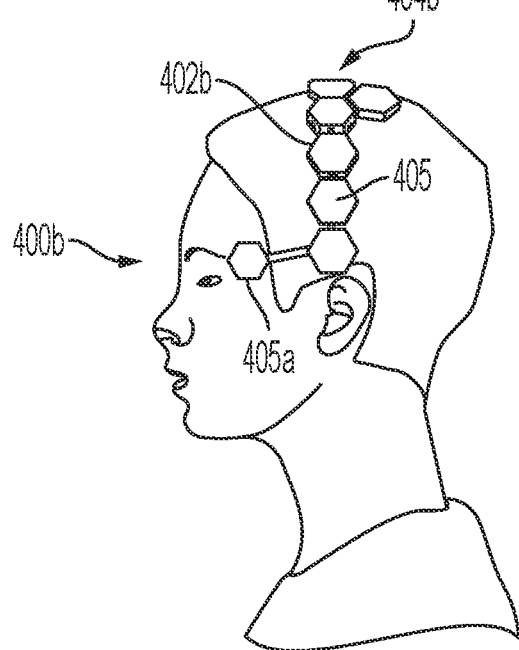
FIG. 4B illustrates a system configured to record neurostimulation information acquired using transcranial sensing of a subject's brain in accordance with various embodiments.

FIG. 4B illustrates a system 400b configured to record neurostimulation information acquired using transcranial sensing of a subject's brain in accordance with various embodiments. The system 400b shown in FIG. 4B can be configured to be the same as or similar to the system 400a illustrated in FIG. 4A. The system 400b includes a support structure 402b configured to support a magnetic sensor arrangement 404b similar that shown in FIG. 4A. The support structure 402b is configured to support an array of magnetic sensors 405 and additional magnetic sensors 405a positioned near the subject's temples and configured for sensing local magnetic fields emanating from a specified brain region or regions proximate the subject's temples. For example, the magnetic sensors 405 can be mounted to the support structure 402b relative to specific regions of the subject's olfactory system, including the olfactory cortex and the piriform cortex, and the additional magnetic sensors 405a can be mounted to the support structure 402b relative to the olfactory bulb located near the front of the brain in both cerebral hemispheres.

Figure 5:
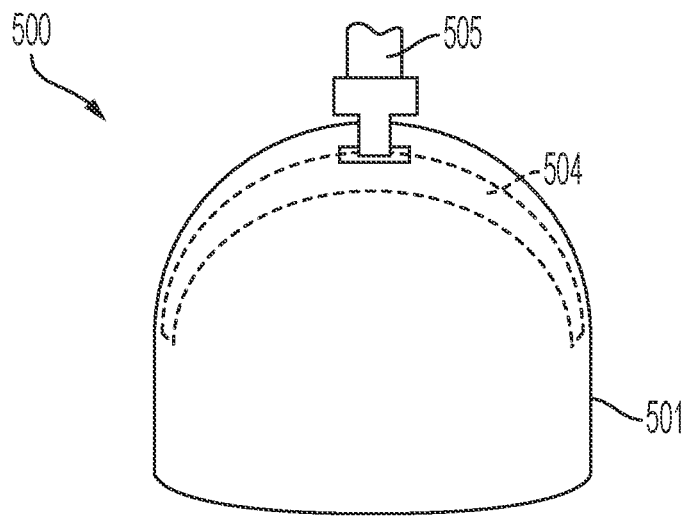
FIG. 5 illustrates a support structure configured to support a magnetic sensor arrangement in accordance with various embodiments.

FIG. 5 illustrates a support structure 502 configured to support a magnetic sensor arrangement 504 in accordance with various embodiments. The support structure 502 shown in FIG. 5 includes a helmet structure 502 within which an array of magnetic sensors 504 is mounted (individual magnetic sensors not shown). The helmet structure 502 is configured to be raised and lowered by an external mechanism relative to the subject's head when the subject is at a stationary (e.g., non-ambulatory) position. For example, the subject may be sitting in the chair of a test station and the helmet structure 502 can be lowered and raised relative to the subject's head via a coupling member 505 mechanically coupled to an external mechanism (e.g., a controllable manual or electromechanical lift mechanism).

Figure 6A:
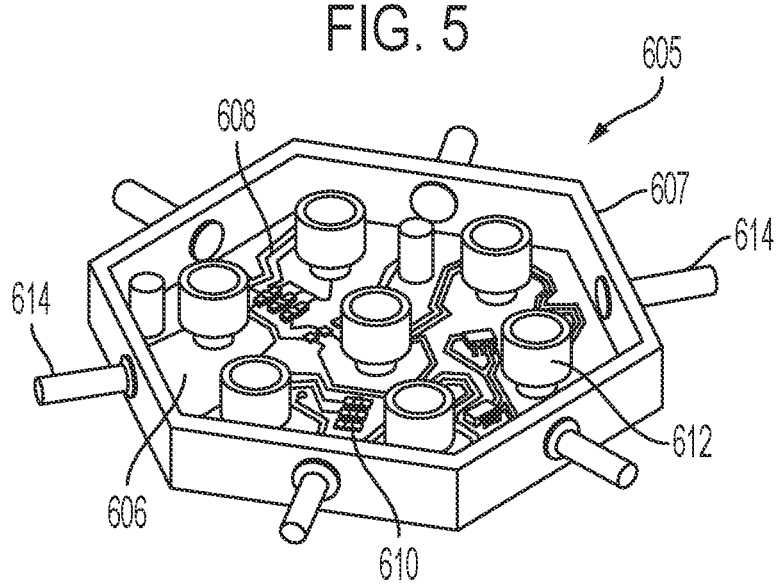
FIG. 6A illustrates a magnetic sensor suitable for use in any of the magnetic sensor arrangements disclosed herein in accordance with various embodiments.

FIG. 6A illustrates a magnetic sensor 605 suitable for use in any of the magnetic sensor arrangements disclosed herein in accordance with various embodiments. The magnetic sensor 605 shown in FIG. 6A includes mechanical features configured to establish an interlocking relationship with one or more other magnetic sensors 605 of a magnetic sensor arrangement (e.g., magnetic sensor arrangement 404a, 404b shown in FIGS. 4A and 4B). The magnetic sensor 605 includes a chassis 607 within which a printed circuit board (PCB) 606 is disposed. One or more magnetic sensor elements 612 are positioned on or distributed about the PCB 606. The magnetic sensor 605 can include one or more magnetic sensor elements 612. Each of the magnetic sensor elements 612 can be configured to sense local magnetic fields emanating from a specified region of a subject's brain. The magnetic sensor elements 612 can operate independently or cooperatively with respect to one another. The magnetic sensor elements 612 are communicatively connected to other electronic circuitry (e.g., electronic memory and/or controller) via traces 608 disposed on the PCB 606. The traces 608 can include any combination of signal, control, and power lines. Various passive and active electronic components 610 (e.g., resistors, capacitors, inductors, filters, amplifiers, switches) can be disposed on the PCB 606 and electrically connected to the magnetic sensor elements 612 via the traces 608.

The chassis 607 of the magnetic sensor 605 shown in FIG. 6A includes a multiplicity of interlocking members 614. Typically, the chassis 607 incorporates at least two of the interlocking members 614, but may include more than two interlocking members 614 (e.g., 3, 4, 5, or 6 interlocking members). Each of the interlocking members 614 is configured to be received by a corresponding interlocking member of an adjacent magnetic sensor 605 (not shown, but see FIGS. 6A and 6B). For example, the interlocking members 614 are shown as male connectors in FIG. 6A, which can be received by corresponding female interlocking members (e.g., female connectors) of an adjacent magnetic sensor 605. In some implementations, some of the interlocking members 614 of the magnetic sensor 605 can be male connectors while others can be female connectors.

Figure 6B:
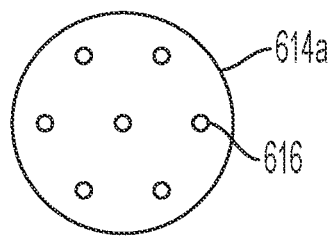
FIG. 6B is a front view of a connection interface of the interlocking members shown in FIG. 6A in accordance with various embodiments.

FIG. 6B is a front view of a connection interface 614a of the interlocking members 614 shown in FIG. 6A in accordance with various embodiments. The connection interface 614a includes a number of connector elements (e.g., pins, ports, and/or receptacles) configured to provide electrical connectivity and optical connectivity (optional in some embodiments) between the PCB 606 of the magnetic sensor 605 and other electronic circuitry (e.g., PCBs 606 of adjacent magnetic sensors 605, an electronic memory, and/or controller). The interlocking mechanical and electrical/optical features of the magnetic sensor 605 provide for enhanced flexibility in terms of the number, configuration, and positioning of a multiplicity of magnetic sensors 605 that define a magnetic sensor arrangement in accordance with various embodiments. For example, the interlocking mechanical and electrical/optical features of the magnetic sensors 405 shown in FIGS. 4A and 4B provide for the addition of two extra magnetic sensors 405a positionable relative to a subject's left and right temples.

Figure 7:
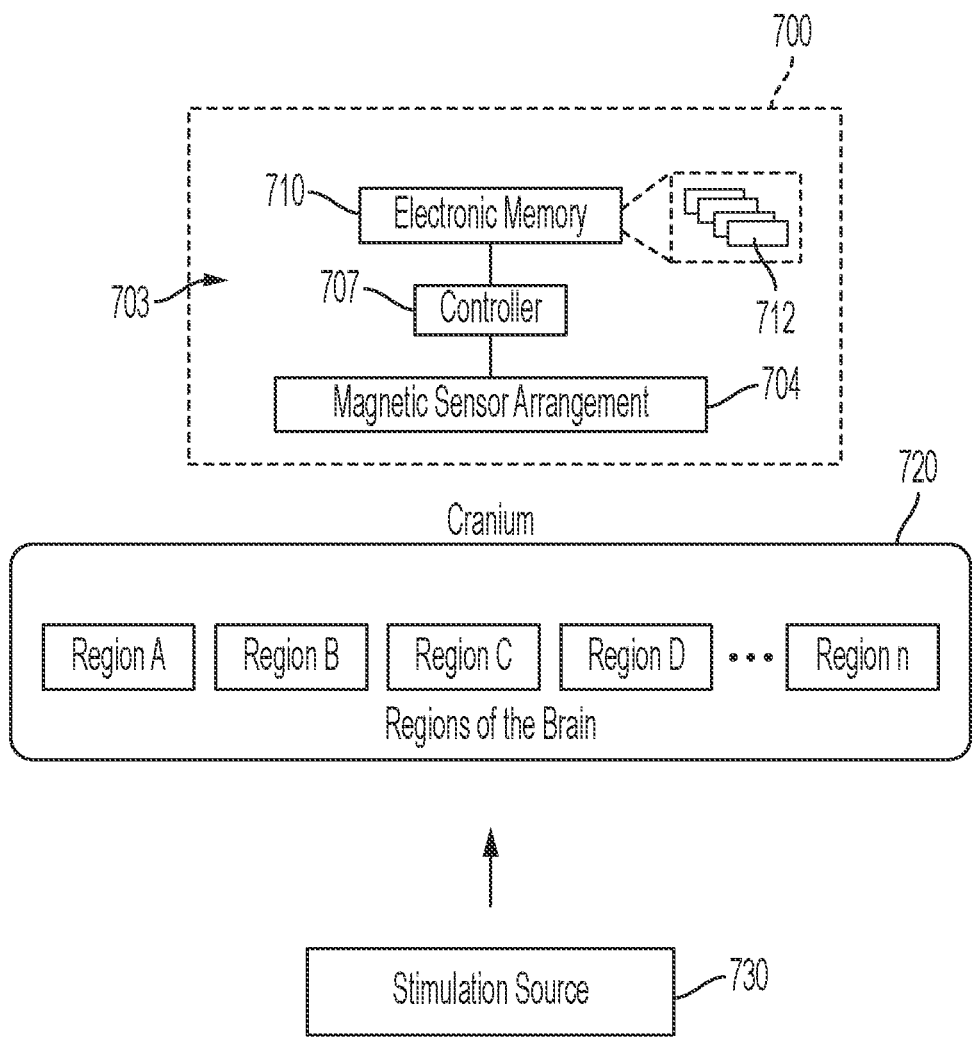
FIG. 7 illustrates a system configured to record neurostimulation information acquired using transcranial sensing of a specific region or regions a subject's brain in accordance with various embodiments.

FIG. 7 illustrates a system 700 configured to record neurostimulation information acquired using transcranial sensing of a specific region or regions a subject's brain in accordance with various embodiments. The system 700 includes a support structure 702 configured for placement on or about a subject's head. The system 700 includes an electronic recording apparatus 703 which includes a magnetic sensor arrangement 704 and an electronic memory 710. The electronic recording apparatus 703 also includes a controller 707 operatively coupled to the magnetic sensor arrangement 704 and the electronic memory 710. The controller 707 is configured to control operation of the system 700 and, in some embodiments, effect communication and interaction with an external system or device (e.g., via a wired or wireless communication device (not shown) coupled to the controller 707). As was previously discussed, the electronic memory 710 is configured to store various spatiotemporal patterns 712.

The magnetic sensor arrangement 704 is configured for transcranial sensing of local magnetic fields emanating from a specific region of a subject's brain. For example, the magnetic sensor arrangement 704 can be configured for transcranial sensing of local magnetic fields emanating from any one or more of Regions A-n of a subject's brain 720. Each of Regions A-n can be representative of a region associated with one or more of the subject's sense organ or organs, vestibular system, and/or memory. For example, each of Regions A-n can represent a region or regions of the brain 720 associated with one or more of the following sensory organs: eyes, ears, skin, vestibular system, nose, and mouth/tongue, which contribute, respectively, to the sensory perceptions of vision, hearing, touch, spatial orientation, smell, and taste. Regions A-n can also represent a region or regions of the brain 720 associated with short-term and/or long-term memory.

For example, Region A can represent regions of the brain 720 associated with a subject's nose/olfactory system and sensory perception of smell (e.g., frontal lobe, olfactory cortex, piriform cortex, olfactory bulb). Region B can represent regions of the brain 720 associated with a subject's eyes/vision system and sensory perception of vision (e.g., occipital lobe, parietal and temporal lobes). Region C can represent regions of the brain 720 associated with a subject's auditory system and sensory perception of hearing (e.g., temporal lobe, auditory cortex: primary A1, secondary A2, and tertiary A3 regions). Region D can represent regions of the brain 720 associated with a subject's somatosensory system and sensory perception of touch and pressure (e.g., somatosensory cortex primarily, parts of the prefrontal cortex and posterior parietal lobe secondarily).

Region E can represent regions of the brain 720 associated with a subject's gustatory system and sensory perception of taste and flavor (e.g., gustatory cortex, insular cortex, specific portions behind the neocortex, namely the anterior insula, located on the insular lobe, and the frontal operculum, on the frontal lobe). Region F can represent regions of the brain 720 associated with a subject's vestibular system and sensory perception of spatial orientation (e.g., vestibular cortex of the cerebellum, the core region, parietoinsular vestibular cortex (PIVC), located in the posterior insula and retroinsular region and including the parietal operculum). Other regions of the subject's brain 720 not specifically associated with one of the subject's senses can be subject to transcranial sensing of local magnetic fields using the system 700. For example, Region G can represent regions of the brain 720 associated with short-term and/or long-term memory (e.g., hippocampus, amygdala, cerebellum, prefrontal cortex).

As is shown in FIG. 7, a specified region or regions of a subject's brain 720 can be stimulated via a stimulation source 730. The stimulation source 730 will vary depending on the subject's sensory system being evaluated using the system 700. For example, the stimulation source 730 may involve manual or automated delivery of one or more odors, one or more visual stimuli (e.g., colors, images, video, graphics), one or more auditory stimuli (natural and man-made sounds, music, tones), different forms of touch and/or pressure to specific body locations, one or more flavors or tastes (e.g., sweet, sour, bitter, salty, umami), and various semantic and episodic memory tests (e.g., neuropsychological tests).

In response to delivery of a stimulus or stimuli by the stimulation source 730, the magnetic sensor arrangement 704 senses local magnetic fields emanating from a specified region or regions of the subject's brain 720. The sensed local magnetic fields acquired by the magnetic sensor arrangement 704 correspond to patterns of stimulation of the specified region or regions of the subject's brain 720 caused by stimulating one or more of the subject's sense organ or organs, vestibular system, and/or memory. The electronic memory 710 is configured to store a multiplicity of patterns 712 of neurostimulation data associated with delivery of the stimulus or stimuli by the stimulation source 730. Each of the patterns 712 stored in the electronic memory 710 can correspond to neural activity responsive to a specific one of the stimuli delivered by the stimulation source 730.

The controller 707 is configured to coordinate the operation of the system 700 including activation and deactivation of the magnetic sensor arrangement 704 and storing of neurostimulation data in the electronic memory 710. The controller 707 can be configured to receive a manual activation input concurrently or shortly after manual or automated activation of the stimulation source 730. Alternatively, the controller 707 can be configured to receive a control signal directly from the stimulation source 730 which causes activation of the system 700 concurrently with or shortly after manual or automated activation of the stimulation source 730.

Figure 8:
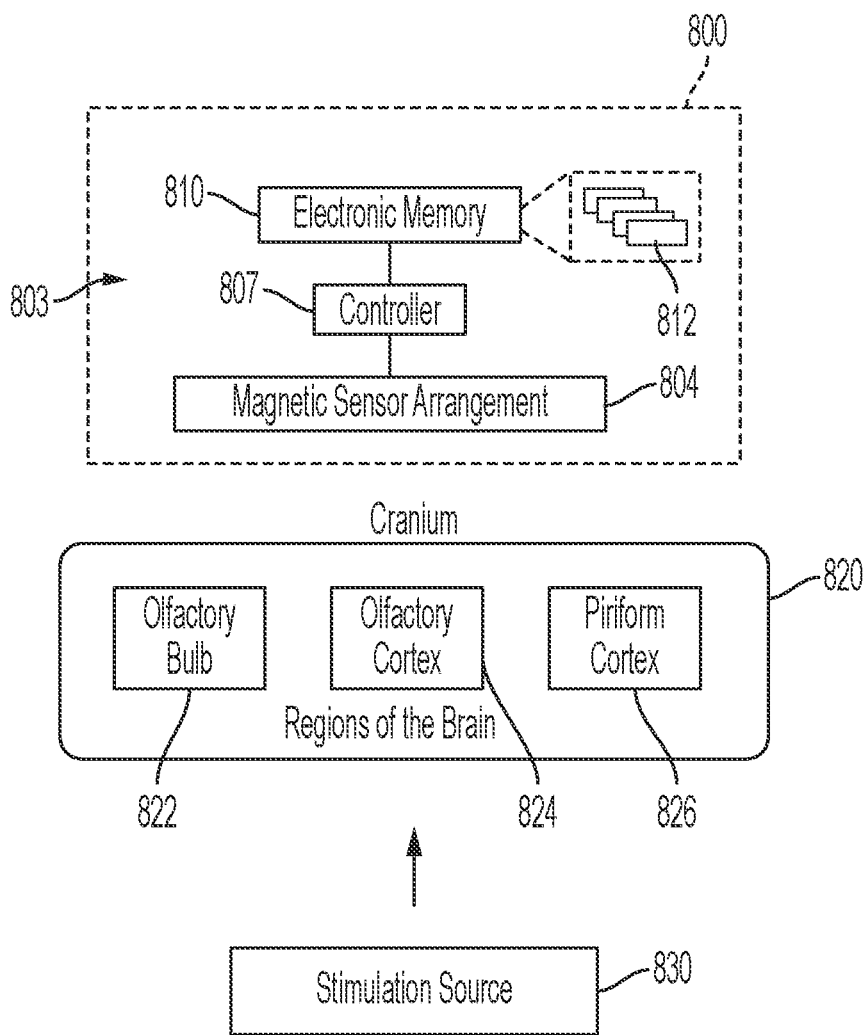
FIG. 8 illustrates a system configured to record neurostimulation information acquired using transcranial sensing of a specific region or regions a subject's olfactory system in accordance with various embodiments.

FIG. 8 illustrates a system 800 configured to record neurostimulation information acquired using transcranial sensing of a specific region or regions a subject's olfactory system 820 in accordance with various embodiments. The system 800 includes a support structure 802 configured for placement on or about a subject's head. The system 800 includes an electronic recording apparatus 803 which includes a magnetic sensor arrangement 804 and an electronic memory 810. The electronic recording apparatus 803 also includes a controller 807 operatively coupled to the magnetic sensor arrangement 804 and the electronic memory 810. The controller 807 is configured to control operation of the system 800 and, in some embodiments, to control communication and interaction with an external system or device (e.g., via a wired or wireless communication device (not shown) coupled to the controller 807). As was previously discussed, the electronic memory 810 is configured to store various spatiotemporal patterns 812.

The magnetic sensor arrangement 804 is configured for transcranial sensing of local magnetic fields emanating from the subject's olfactory system 820 of the brain. For example, the magnetic sensor arrangement 804 can be configured for transcranial sensing of local magnetic fields emanating from any one or more of the subject's olfactory bulb 822, olfactory cortex 824, and piriform cortex 826.

As is further shown in FIG. 8, the subject's olfactory system 820 can be stimulated via a stimulation source 830. The stimulation source 830 can be configured to expose the subject to one or more predetermined odors. In response to delivery of each predetermined odor of odors via stimulation source 830, the magnetic sensor arrangement 804 senses local magnetic fields emanating from one or more of the subject's olfactory bulb 822, olfactory cortex 824, and piriform cortex 826. The sensed local magnetic fields acquired by the magnetic sensor arrangement 804 correspond to patterns of stimulation of the subject's olfactory bulb 822, olfactory cortex 824, and piriform cortex 826 caused by exposing the subject to one or more predetermined odors. The electronic memory 810 is configured to store a multiplicity of patterns 812 of neurostimulation data associated with delivery of the one or more predetermined odors. Each of the patterns 812 stored in the electronic memory 810 can correspond to neural activity response to a specific one of the predetermined odor or a combination of predetermined odors delivered by the stimulation source 830.

The controller 807 is configured to coordinate the operation of the system 800 including activation and deactivation of the magnetic sensor arrangement 804 and storing of neurostimulation data in the electronic memory 810. The controller 807 can be configured to receive a manual activation input concurrently or shortly after manual or automated activation of the stimulation source 830. Alternatively, the controller 807 can be configured to receive a control signal directly from the stimulation source 830 which causes activation of the system 800 concurrently with or shortly after manual or automated activation of the stimulation source 830.

Figure 9:
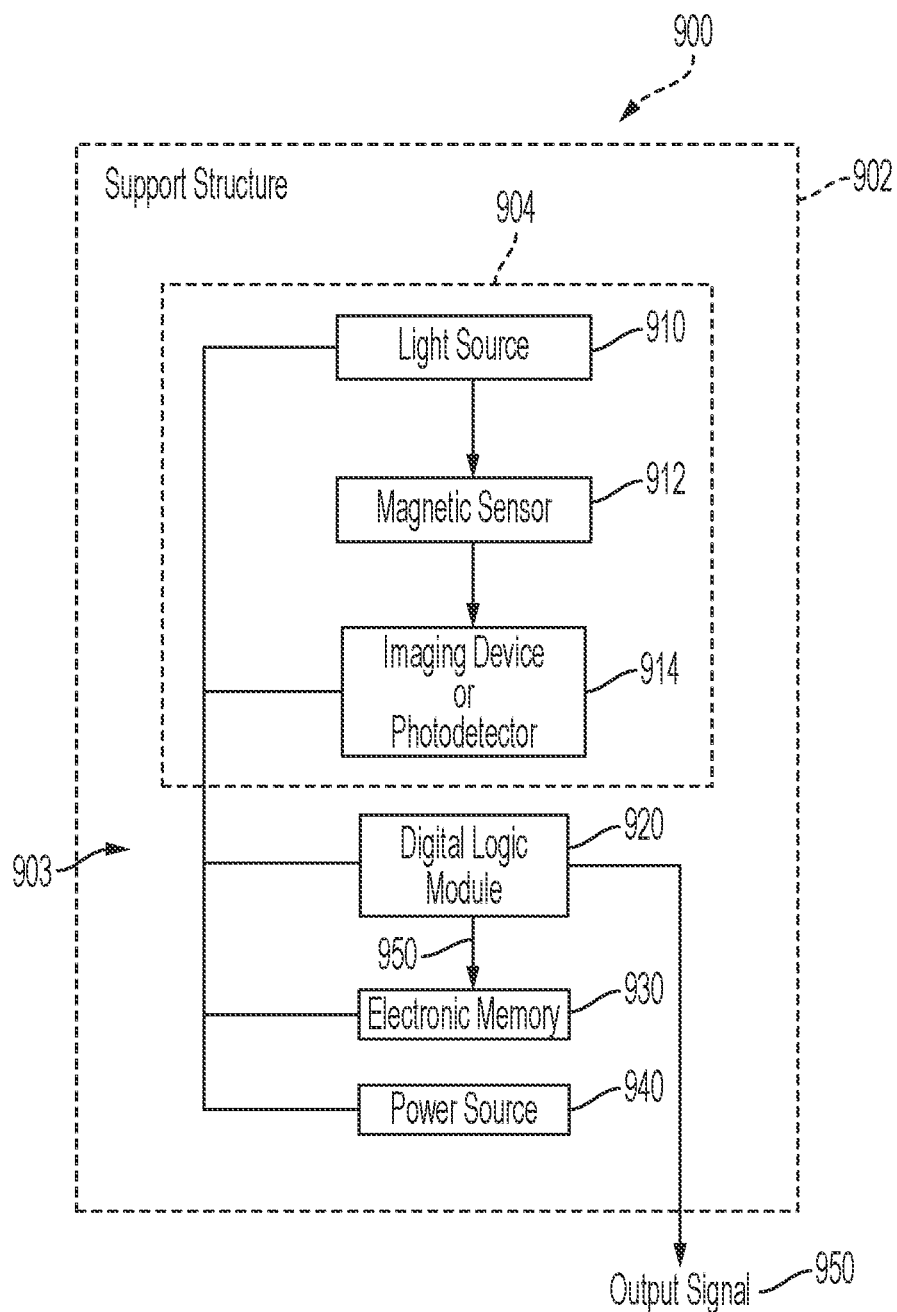
FIG. 9 illustrates a system configured to record neurostimulation information acquired using transcranial sensing of a specific region or regions a subject's brain in accordance with various embodiments.

FIG. 9 illustrates a system 900 configured to record neurostimulation information acquired using transcranial sensing of a specific region or regions a subject's brain (e.g., olfactory system) in accordance with various embodiments. The system 900 includes a support structure 902 configured for placement on or about a subject's head. The system 900 includes an electronic recording apparatus 903 which includes one or a multiplicity of magnetic sensor arrangements 904, a digital logic module 920 (e.g., a controller, processor or other logic device), an electronic memory 930, and a power source 940 (e.g., one or more lithium-ion batteries). As discussed previously, the system 900 can include a multiplicity of the magnetic sensor arrangements 904 arranged in the form of an array. In such embodiments, each of the multiplicity of magnetic sensor arrangements 904 is operatively coupled to the digital logic module 920, the power source 940, and the electronic memory 930 via the digital logic module 920 and a communication bus. It is understood that the electronic memory 930 can be separate from, or integral to, the digital logic module 920.

The digital logic module 920 is configured to control operation of the system 900 and, in some embodiments, effect communication and interaction with an external system or device (e.g., via a communication device (not shown) coupled to the digital logic module 920). As was previously discussed, the electronic memory 930 is configured to store various spatiotemporal patterns. The magnetic sensor arrangement 904 is configured for transcranial sensing of local magnetic fields emanating from one or more specified regions (e.g., the olfactory system) of the subject's brain.

The magnetic sensor arrangement 904 includes a light source 910, such as a laser. Light generated by the light source 910 is directed to a magnetic sensor 912. An imaging device (e.g., CCD sensor, active-pixel sensors (CMOS sensor), charge injection devices (CID device)) or photodetector 914 is configured to detect an optical response of the magnetic sensor 912 to the light generated by the light source 910. In some embodiments, the magnetic sensor arrangement 904 is configured as an optically pumped magnetometer. In other embodiments, the magnetic sensor arrangement 904 is configured as an magnetometer arrangement comprising an NV center diamond crystal. The digital logic module 920 is configured to receive an output signal from the imaging device or photodetector 914.

In the case of an imaging device 914, the output signal is typically a digital signal. In the case of a photodetector 914, the output signal may be an analog signal (e.g., output current signal), which can be converted to a digital signal via an analog-to-digital (ADC) circuit integral or coupled to the digital logic module 920. The digital logic module 920 generates an output signal 950 representative of a local magnetic field measurement generated by the magnetic sensor arrangement 904. The output signal 950 is communicated from the digital logic module 920 to the electronic memory 930 for storage as one of a multiplicity of patterns of stimulation of a specified region or regions of the subject's brain caused by stimulating one or more of the subject's sense organ or organs, vestibular system, and/or memory. The output signal 950 can also be communicated to a system or device external of the system 900.

According to an embodiment of a magnetic sensor arrangement 904 configured as an OPM sensor, the light source 910 includes a laser, the magnetic sensor 912 includes a glass vapor cell containing sensing atoms in a gaseous state, and a photodetector 914. The OPM sensor 904 can be configured as a Zero-Field OPM sensor or a Total-Field OPM sensor. The OPM 904 configured as a Zero-Field OPM sensor can exhibit extreme sensitivity when the magnetic background is small, works in low field environments, and measures the vector components of the field. When the field is nearly zero, the atoms in the vapor cell become mostly transparent allowing maximum light onto the photodetector 914. Any change in the field induces a change in the transparency of the atoms. The resulting change in the photocurrent gives a measure of the magnetic field signal. The Zero-Field OPM sensor can measure field components along the sensitive axes and provides ultra-high sensitivity for detecting very weak magnetic fields, such as local magnetic fields emanating from one or more specified regions of the subject's brain indicative of activation and/or suppression of neuronal activities. A suitable Zero-Field OPM sensor for use in the magnetic sensor arrangement 904 is disclosed in U.S. Pat. No. 10,775,450, which is incorporated herein by reference.

The OPM sensor 904 configured as a Total-field OPM sensor can operate in Earth's field with high accuracy, measures the scaler amplitude of the field, and does not need calibration. The atoms in the vapor cell have a well-defined resonance frequency that is directly proportional to the magnitude of the field being measured. Internal coils apply a varying RF field to resolve this frequency by monitoring the transmitted light through the cell. Resonance is achieved when absorption is maximized. The output of the Total-Field OPM sensor is the value of this RF frequency, multiplied by a known scaling factor which directly converts frequency to magnetic field. A suitable Total-Field OPM sensor for use in the magnetic sensor arrangement 904 is disclosed in U.S. Published Patent Application No. 2018/0238974, which is incorporated herein by reference.

Figure 10A:
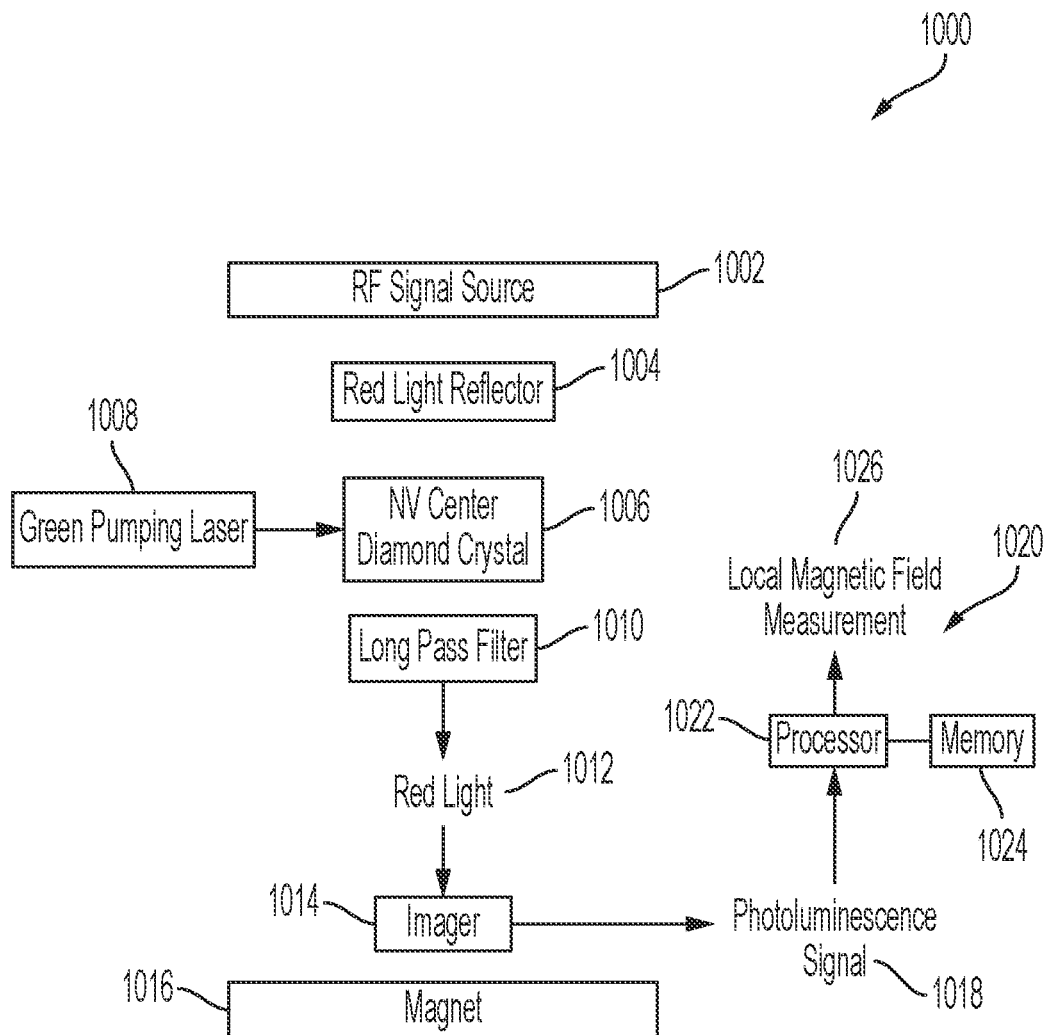
FIG. 10A illustrates a magnetic sensor arrangement comprising a nitrogen-vacancy (NV) center diamond crystal magnetic sensor in accordance with various embodiments.
Figure 11:
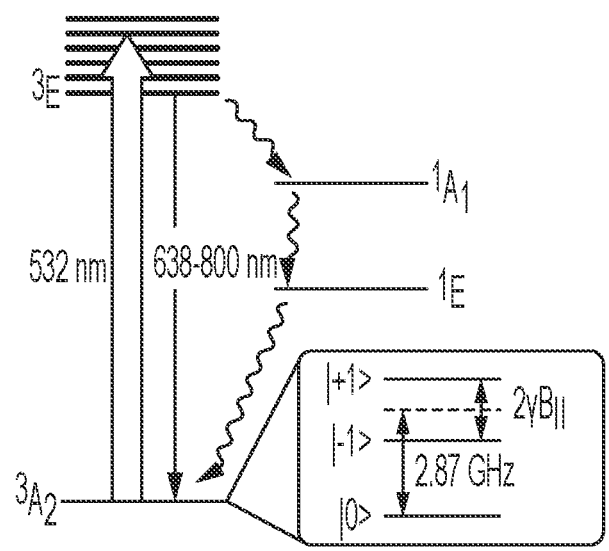
FIG. 11 illustrates an operational principle of an NV center diamond crystal magnetic sensor in accordance with one embodiment.

FIG. 10A illustrates a magnetic sensor arrangement 1000 comprising an NV center diamond crystal magnetic sensor in accordance with various embodiments. A nitrogen vacancy or NV center is an atomic-scale point defect in a diamond crystal lattice. A nitrogen atom substitutes for a carbon atom in the diamond lattice and forms a nearest neighbor pair with a lattice vacancy. In some cases, the NV center attracts an additional electron and it and an unbound electron from the vacancy form a spin 1 pair with quantized energy levels as shown in the example of FIG. 11. The photoluminescence intensity of the NV center diamond crystal is proportional to the relative population of the spin 1 and spin 0 energy levels because the excitation is spin conserving and the spin 1 first excited state has a non-radiative decay path. Microwave radiation at an energy equal to the splitting of the spin 1 and spin 0 ground states can change the population of each of these states driving spin 0 electrons into the spin 1 state.

An applied magnetic field splits the degeneracy in the spin +1 and spin −1 states which shifts the energy splitting between the spin 0 and spin −1 states. Consequently, by exciting the NV center diamond crystal with laser light (e.g. green laser light) and concurrently sweeping the applied microwave frequency, the local magnetic field can be measured at the NV center diamond crystal directly from the frequency value where the photoluminescence signal drops. In a luminescence vs microwave frequency graph, there will be two "dips" for each NV center, which correspond to the energy between the spin −1 and spin 0 states and the spin 1 and spin 0 states. In addition, regarding FIG. 11, it should be understood that y represents a physical constant. It should further be understood that the frequency depends on the magnetic field parallel to the defect axis, represented by $B_{//}$.

The magnetic sensor arrangement 1000 includes a green pumping laser 1008 configured to excite nitrogen vacancy centers of a diamond crystal (e.g., an NV center diamond crystal) 1006. A long pass filter 1010 is configured to filter a red light 1012 caused by the excitation of the NV centers of the diamond crystal 1006 through to an image sensor 1014 which, in turn, creates a photoluminescence signal 1018. In some embodiments, the image sensor 1014 is pixelated to provide a spatially resolved magnetic field image. The long pass filter 1010 is stacked between the NV center diamond crystal 1006 and the image sensor 1014. For example, the long pass filter 1010 and the image sensor 1014 can be connected with an adhesive that is transparent for red light. It is noted that the long pass filter 1010 and the NV center diamond crystal 1006 can be glued together with an adhesive that blocks green laser light. It is further noted that the long pass filter 1010 can instead be configured as a bandpass filter, and absorption filter, or an interference filter. In some implementations, a red light reflector 1004 can be stacked on a surface of the NV center diamond crystal 1006 opposing a surface of the NV center diamond crystal 1006 stacked on the long pass filter 1010. In some embodiments, a plurality of NV center diamond crystals 1006 can be attached across a face of the image sensor 1014 and arranged such that green laser light of the green pumping laser 1008 is totally internally reflected with a single crystal and transmitted with minimal loss to a neighboring crystal to make a large area magnetic imaging sensor.

A radio frequency source 1002 (e.g., an RF coil) is configured to apply radiation to the NV center diamond crystal 1006. The RF source 1002 may also be configured to shift energy of the photoluminescence signal 1018. In some implementations, the RF source 1000 can be stacked on a mirror stacked on the NV center diamond crystal 1006. The RF source 1000 can be configured to drive electron population transitions and read out a local projection of a magnetic field along a center crystallographic axis of the NV center defects of the NV center diamond crystal 1006. A magnet 1016 is configured to break a degeneracy of the NV centers. The components of the magnetic sensor arrangement 1000 shown in FIG. 10A advantageously provide for a compact device, in large part due to stacking the long pass filter 1010 between the NV center diamond crystal 1006 and the image sensor 1014.

The photoluminescence signal 1018 produced by the magnetic sensor arrangement 1000 can be communicated to a digital logic module 1020 which, in the embodiment shown in FIG. 10A, includes a processor 1022 operatively coupled to memory 1024. In some embodiments, the digital logic module 1020 is integral to the magnetic sensor arrangement 1000. In other embodiments, the digital logic module 1020 is separate from, but operatively coupled to, the magnetic sensor arrangement 1000. The memory 1024 is configured to store computer program code which, when executed by the processor 1022, causes the digital logic module 1022 to measure a local magnetic field 1026 by measuring a frequency of a radiation where the photoluminescence signal drops.

Figure 10B:
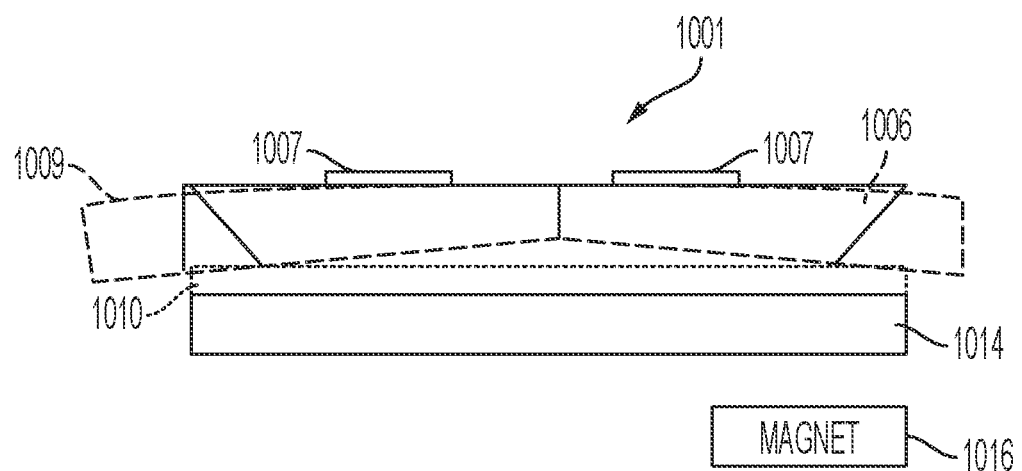
FIG. 10B shows a compact magnetic sensor arrangement comprising a nitrogen-vacancy (NV) center diamond crystal magnetic sensor in accordance with one embodiment.

FIG. 10B shows a compact magnetic sensor arrangement 1001 in accordance with one embodiment. As illustrated in FIG. 10B, and with continued reference to FIG. 10A, a diamond crystal 1006 with implanted NV center defects and an optical long pass filter 1010 are stacked directly on a pixelated image sensor 1014. Green laser light is coupled in from a side 1009 of the diamond crystal 1006 via edge coupling and totally internally reflected within the diamond crystal 1006 to excite the NV center bound state electrons while minimizing the green background in the photoluminescence measurement. NV centers emit light isotropically in all directions. A red light reflector 1004 is included on the diamond crystal surface opposite the long pass filter 1010 to reflect light back towards the image sensor 1014 and double the collection efficiency. This reflector 1004 can optionally be omitted if spatial resolution is more critical that signal sensitivity. An integrated RF coil 1002 is included on top of the mirror diamond surface to drive the electron population transitions and readout the local projection of the magnetic field along the NV center's crystallographic axis. As the frequency is swept, a series of pairs of dips each corresponding to a NV center projection can be seen. In addition, a magnet 1016 (either permanent or electromagnet) is included to break the degeneracy of the NV ensemble projections and spectrally separate the dips in the photoluminescence vs. RF frequency plot.

Because the magnet 1016 may suitably be placed in different locations, a specific location of the magnet is not shown in FIG. 10B. The device stack up includes: optional top red light reflector 1004, NV center diamond crystal 1006, long pass filter 1010, and the image sensor 1014. In some embodiments, any or all of the components can be connected with no gap either by direct deposition (e.g., sputtering an aluminum mirror on the top surface of the diamond substrate). In other embodiments, any or all of the components can be coupled with a high index adhesive that is transparent for red light. If an adhesive that is transparent for red light and opaque for other colors of light is used, this could combine the purpose of the long pass filter 1010 and the adhesive, and thus eliminate the need for using a long pass filter 1010 which would eliminate some thickness and thereby improve resolution.

Matching the index of the adhesive material to diamond crystal's index (n=2.4) can improve the spatial resolution and light collection efficiency. The highest possible index adhesive that still meets the transparency requirements should be used. In one example, an optically clear adhesive with an index of about 1.4 is used. It should be understood that if an adhesive is not used, there might be an air gap (e.g., where the adhesive would otherwise be between the various layers of diamond crystal 1006, long pass filter 1010, and image sensor 1014) along at least a portion of contacting layers. In some embodiments, between layers where no adhesive is used, there is no purposely created space but air gap(s) still exist along certain portions of the edges. In some aspects, the airgap is a nuisance because its presence can create some diffusion in the light signal that decreases spatial resolution. Thus, in some exemplary embodiments, there is no airgap. In some embodiments, the long pass filter 1010 is pressed to the imager 1014 (instead of gluing it), in which case a small airgap may be unavoidable.

There are many options for the components described above, and the examples given are not meant to limit the design variations. For example, various long pass filters or other filters may be used. In this regard, a purpose of the long pass filter 1010 is to block the (532 nm) green laser light. For example, in some embodiments, the filter 1010 passes 639-800 nm light and blocks 532 nm light (e.g., the filter 1010 may be a bandpass filter). In another example, the filter 1010 may be a long pass filter. In one aspect, the filter 1010 can be an absorption filter or an interference filter. The filter 1010 can be directly deposited onto the NV center diamond crystal 1006 or glued to the diamond crystal 1006 with a high index adhesive that is also transparent in certain wavelength ranges (e.g., 639-800 nm) such that the green laser light is blocked.

Similarly, the top red light reflector 1004 can be implemented with a broad band reflector (mirror) or low frequency reflector that reflects light in a particular band such as the 639-800 nm band. The reflector 1004 can be deposited directly on the NV center diamond crystal 1006 or glued to the diamond crystal 1006 with a high index adhesive.

The image sensor 1014 can be any light-to-charge converter and can be pixelated or not. Examples include complementary metal-oxide semiconductor (CMOS) imagers, charge-coupled device (CCO) imagers, and large area thin film transistor/photodiode imagers. In some embodiments of this compact system 1001, the spatial resolution will be limited by the larger of the thickness of the optical stack (diamond crystal 1006 and long pass filter 1010) or the imager pixel. The diamond crystal 1006 minimum thickness is set by the mechanical stability of the diamond crystal 1006 and the thickness needed to achieve good coupling for the green excitation laser. A suitable NV center diamond crystal 1006 can have a thickness of about 250 um with a polished edge 1009 to serve as an edge coupling of the totally internally reflected laser light. If an imager 1014 with pixels smaller than the optical stack thickness is selected, pixel binning up to the size of the optical stack can be done to increase the signal size with no loss of resolution.

In some embodiments, the thickness of the diamond crystal 1006 is the same or about the same as the pixel size of the image sensor 1014. The overall imaging area will also be limited by the size of the diamond crystal 1006. NV diamond crystals 1006 as large as about 4 mm×4 mm have been demonstrated in the art, but larger crystals may be possible. The size of the available diamond crystal 1006 will impact the choice of image sensor 1014 used in the optical stack. If diamond substrate sizes remain small, a CMOS imager will likely be the best choice. A state of the art 4K 2.8 um pixel CMOS sensor is about 11 mm×11 mm. However, NV diamond crystals 1006 could also be tiled across the surface of an imager 1014 and connected with a high index adhesive to cover a large area. In this case, an a-Si thin-filmtransistor (TFT) imager can be selected as the image sensor 1014 to create a large area, portable, high sensitivity magnetic imager with high spatial resolution.

In some embodiments, the NV centers of the diamond crystal 1006 are near the top surface of the diamond crystal 1006 (e.g., near the red light reflector 1004). In one example, the NV centers are about 5 nm-40 nm from the top surface of the diamond 170. The precise distance depends on the energy of implementation. In other embodiments; the NV centers of the diamond crystal 1006 may be near a bottom surface of the diamond crystal 1006 (e.g., near the long pass filter 1010).

Moreover, NV diamond magnetometers can operate at a room temperature (unlike superconducting quantum interference device (SQUIDs), can measure the vector projections of the magnetic field and, in an ensemble configuration, can provide natural 2-D imaging unlike other sensing technologies which are essentially 0-D point-like sensors.

Embodiments of the magnetic sensor arrangement 1001 illustrated in FIGS. 10A and 10B advantageously add portability to the other benefits of the NV magnetometer imaging system and enable the image sensor 1014 to be used in field environments for non-destructive, non-invasive operation (e.g., in real-time by an ambulatory user) and/or in clinical environments for medical imaging. For example, some embodiments can be used to measure neuron activity (e.g., neurons firing) as described herein by use of a small portable device 1001. In some embodiments, the small portable device 1001 is about 1 inch×1 inch by×1 inch, and uses three conductors, cables and/or traces (e.g., a digital cable for the imager/camera 1014, an RF cable for the RF coil 1002, and a fiber cable for the laser 1008). The small portable device 1001 (e.g., an array of the devices 1001) can easily be strapped to a patient at any suitable location on the patient (e.g., situated on a patient's head via a headband support arrangement as previously described). Embodiments directed to a magnetic sensor arrangement comprising an NV center diamond crystal magnetic sensor can include structures, hardware, software, functionality, and/or processes disclosed in commonly-owned U.S. patent application Ser. No. 16/665,375 filed Oct. 28, 2019, which is incorporated herein by reference in its entirety.

Figure 12:
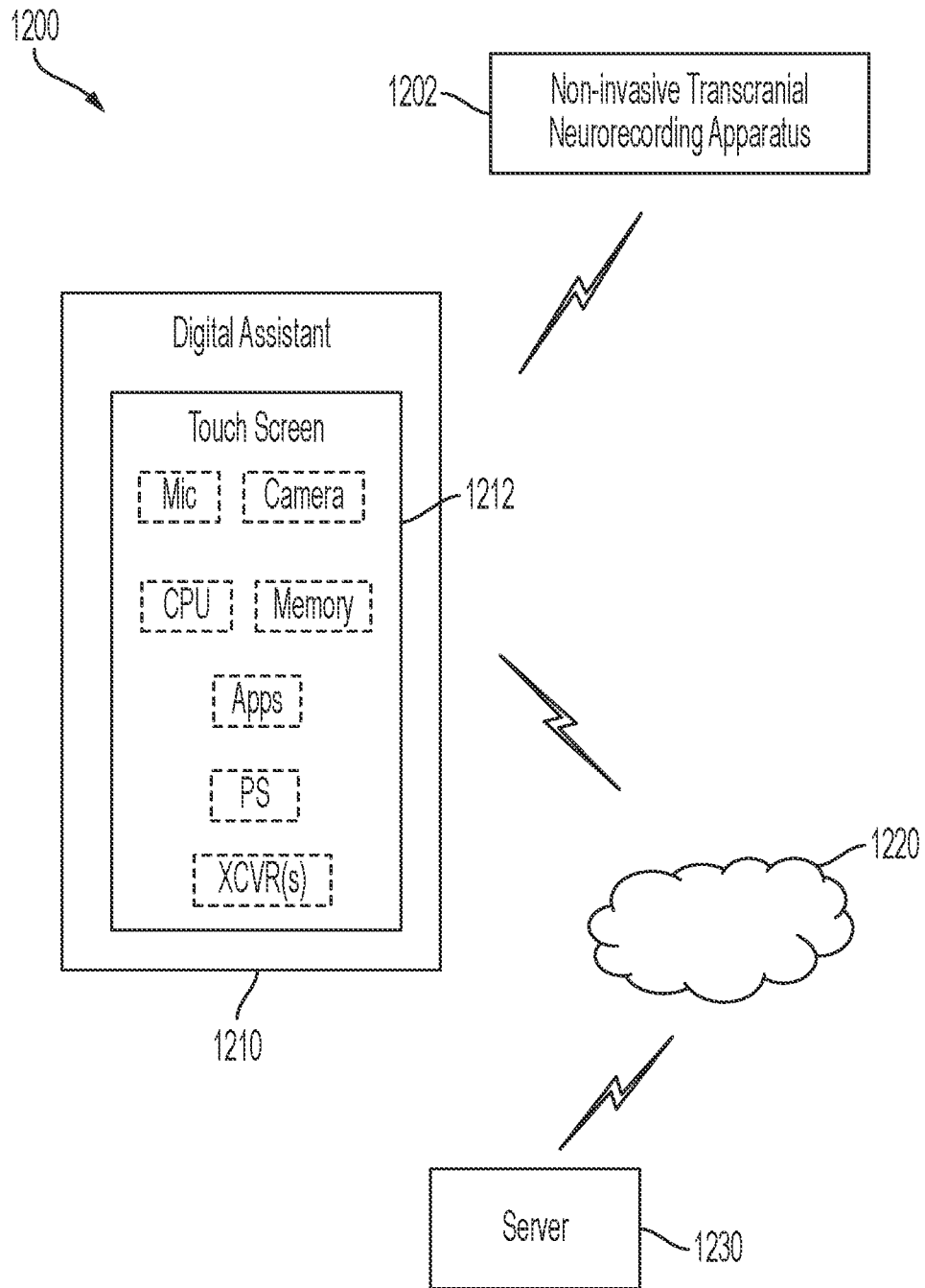
FIG. 12 illustrates a system configured to facilitate implementation of non-invasive transcranial sensing and recording in accordance with various embodiments.

FIG. 12 illustrates a system 1200 configured to facilitate implementation of non-invasive transcranial sensing and recording in accordance with various embodiments. The system 1200 shown in FIG. 12 includes a digital assistant device 1210 configured to communicatively couple to a non-invasive transcranial neurorecording apparatus 1202 and a remote server 1230 via a network connection, such as the Internet 1220. The digital assistant device 1210 can be any mobile or stationary communication device, such as a smartphone, tablet, laptop or desktop PC, for example. The digital assistant device 1210 can include a touchscreen 1212 and a number of conventional components such as a microphone, camera, CPU, memory, power source, one or more radios or wireless transceivers (e.g., WiFi®, Bluetooth®, Zigbee®). The digital assistant device 1210 can also include one or more wired communication ports, such as USB or Ethernet ports. The digital assistant device 1210 includes one or more applications (referred to herein as apps) which can be stored in the memory and are executable by the CPU. At least one of the apps comprises executable instructions or program code that causes the CPU to cooperate with the non-invasive transcranial neurorecording apparatus 1202 in accordance with any of the processes disclosed herein.

In some embodiments, the digital assistant device 1210 cooperates with the server 1232 at least to store data acquired or produced by the non-invasive transcranial neurorecording apparatus 1202 in cloud storage. A cloud processor can provide additional computing resources to process the data received from the digital assistant device 1210 in accordance with the processes (e.g., machine learning) and algorithms disclosed herein. In addition, the cloud processor can generate additional or variant neurorecording data, which can be transferred back to the digital assistance device 1210.

Figure 13A:
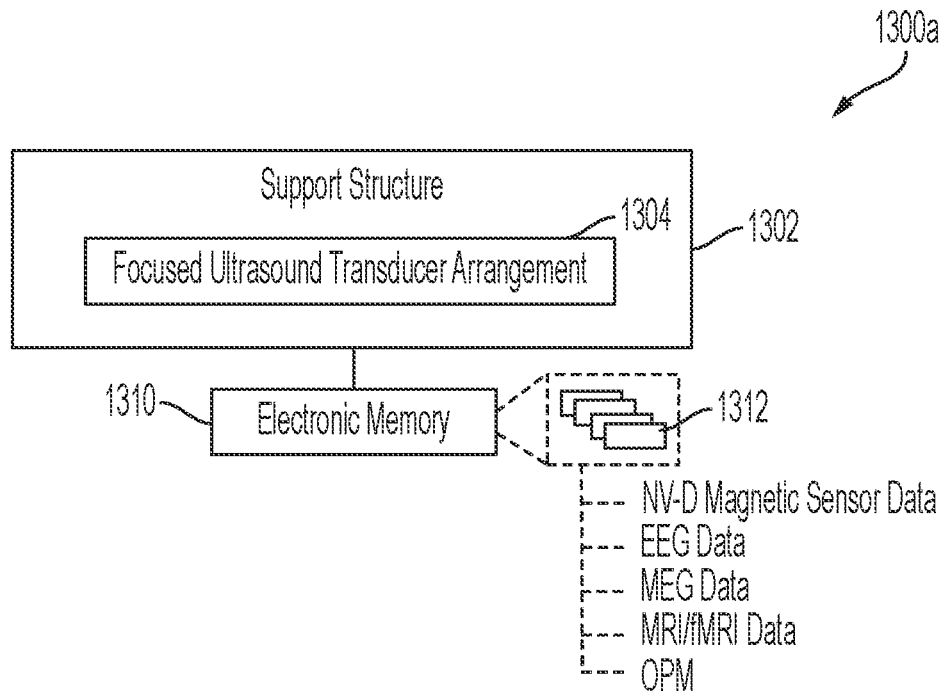
FIGS. 13A and 13B illustrate apparatuses configured to deliver transcranial stimulation to a specified region or regions of a person's brain in accordance with various embodiments.
Figure 13B:
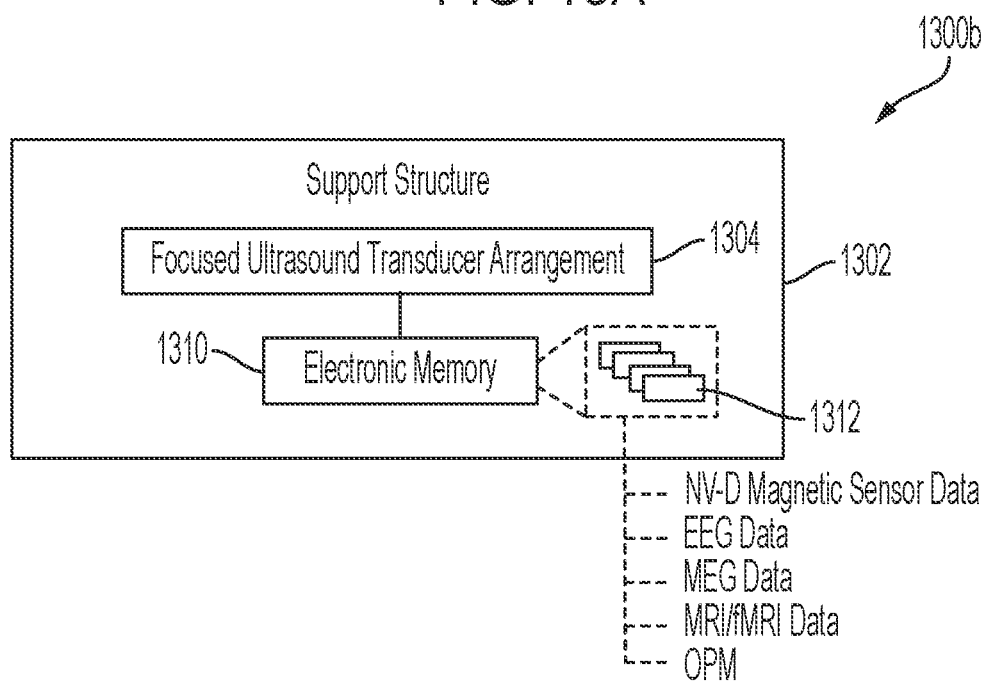

FIGS. 13A and 13B illustrate apparatuses 1300a, 1300b configured to deliver transcranial stimulation to a specified region or regions of a person's brain in accordance with various embodiments. The apparatuses 1300a, 1300b include a support structure 1302 configured for placement on or about a person's head. The support structure 1302 is configured to support at least a focused ultrasound (fUS) transducer arrangement 1304. According to various embodiments, the fUS transducer arrangement 1304 includes an array of ultrasound transducers mounted to the support structure 1302. An electronic memory 1310 is operatively coupled to the fUS transducer arrangement 1304. In the embodiment shown in FIG. 13A, the electronic memory 1310 is not a component of (e.g., not mounted to) the support structure 1302, but is operatively coupled to the fUS transducer arrangement via a wireless or wired connection. In the embodiment shown in FIG. 13B, the electronic memory 1310 is mounted to or supported by the support structure 1302 and operatively coupled to the focused or system transducer arrangement, typically via a wired connection but may alternatively include a wireless connection.

The electronic memory 1310 is configured to store pre-recorded neurostimulation data comprising a multiplicity of patterns 1312 of stimulation of a specified region or regions of a subject's brain. Each of the patterns 1312 is associated with neural activity sensed from a specified region of a subject's brain in response to stimulating one or more of the subject's sense organ or organs, vestibular system, and/or memory to a particular stimulus or particular stimuli as previously described. Each of the patterns 1312 can include stimulation parameters (e.g., a topographic mapping of neural activity amplitude) and a temporal pattern of stimulation (e.g., a temporal mapping of the neural activity).

It is understood that stimulation of a specified region of a subject's brain can refer to one or both of excitation and suppression of neural activity in the specified region of the subject's brain. In the case of suppression, for example, a combination of control over the phase and amplitude of the transcranial ultrasound stimulation can be selected to interfere with the neural activity in the specified region(s) of the subject's brain, such that the net resultant action is the closing of neuronal ion channels and thus the suppression of the region(s) of interest. It is noted that other stimulation modes can used, including a combination of ultrasound and magnetic stimulation, to cancel the potential excitation of a certain region(s) of interest. The patterns 1312 stored in the electronic memory 1310 can be any of the patterns previously described, such as patterns 112 shown in FIGS. 1A-1C. It is also understood that the patterns 1312 stored in the electronic memory 1310 can be representative of patterns 1312 associated with a particular subject's neural activity or a multiplicity (e.g., population) of subjects' neural activity.

In accordance with various embodiments, the patterns 1312 can include neural activity data of various types. For example, the patterns 1312 can include neural activity data acquired from the same or different type of transcranial sensing arrangement. For example, and as previously described, the patterns 1312 can include neural activity data acquired by an NV (nitrogen-vacancy) diamond magnetic sensor arrangement. The patterns 1312 can include neural activity data acquired by an EEG (electroencephalogram) sensor arrangement. The patterns 1312 can include neural activity acquired by and an MEG (magnetoencephalography) sensor arrangement. The patterns 1312 can include neural activity data acquired by an MRI (magnetic resonance imaging) or fMRI (functional magnetic resonance imaging) arrangement. The patterns 1312 can include neural activity data acquired by an optically pumped magnetic (OPM) sensor arrangement. It is understood that the patterns 1312 can include neural activity data acquired from any one or any combination of these and other transcranial sensing arrangements.

According to various embodiments, at least the support structure 1302 and the fUS transducer arrangement 1304 (as well as an on-board power source) are configured to be wearable and portable by a user, such as during ambulatory activities. In some embodiments, the support structure 1302, the fUS transducer arrangement 1304, and the electronic memory 1310 (as well as an on-board power source) are configured to be wearable and portable by a user, such as during ambulatory activities.

Figure 14A:
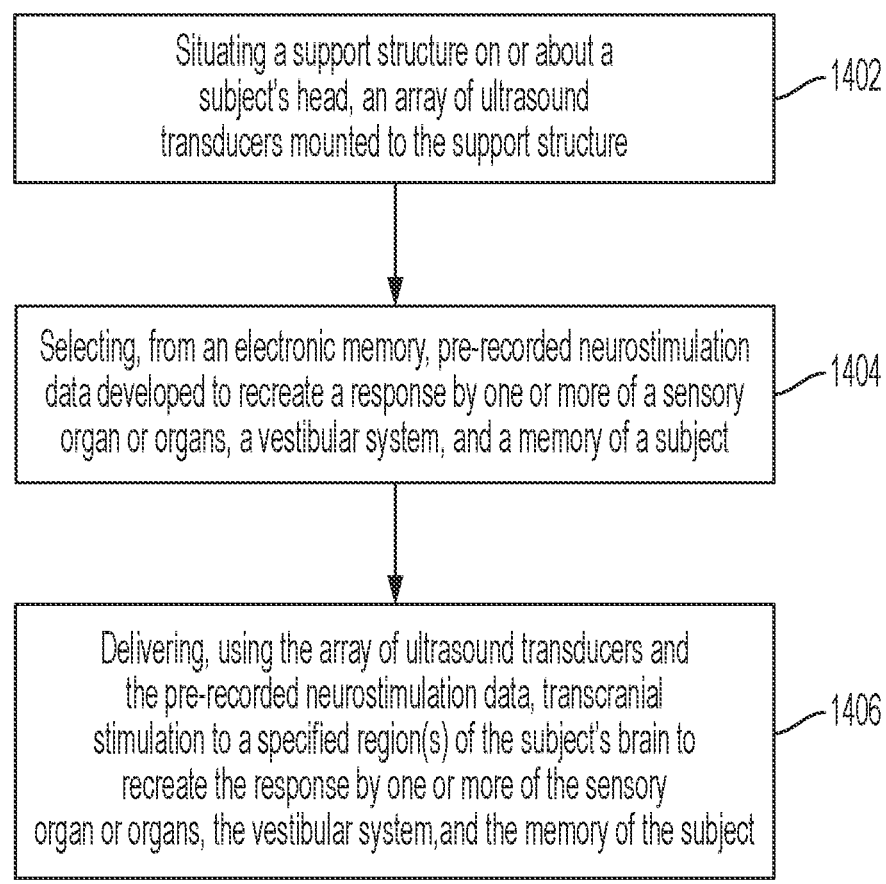
FIGS. 14A and 14B illustrate methods which can be implemented using the apparatuses shown in FIGS. 13A and 13B in accordance with various embodiments.
Figure 14B:
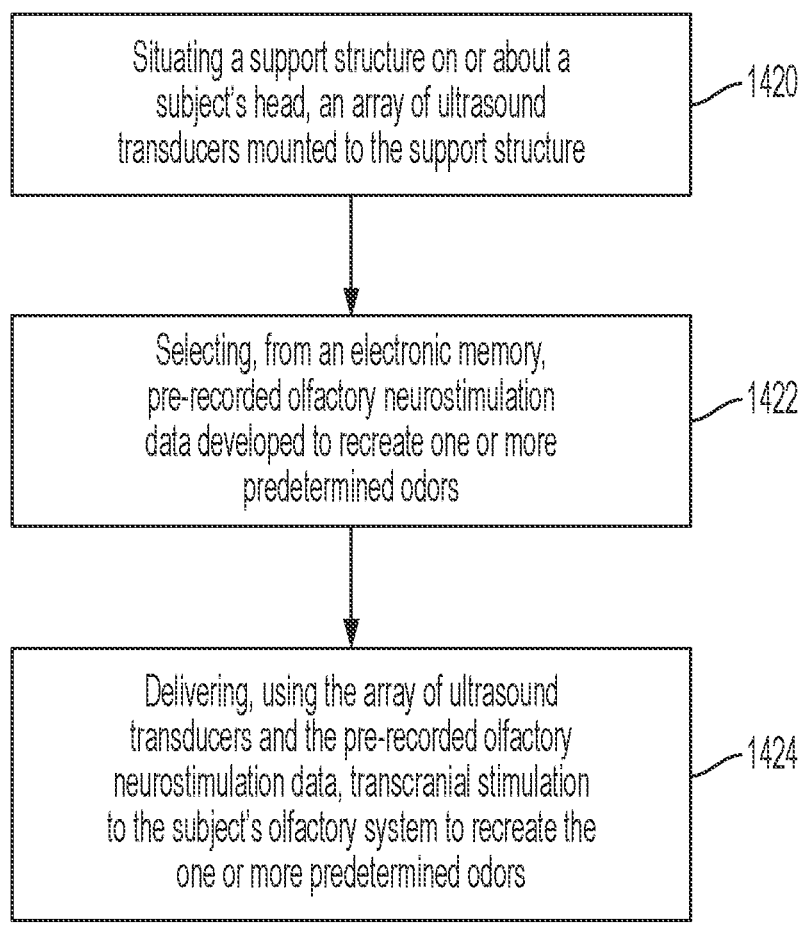

FIGS. 14A and 14B illustrate methods which can be implemented using the apparatuses 1300a, 1300b shown in FIGS. 13A and 13B in accordance with various embodiments. The method shown in FIG. 14A involves situating 1402 a support structure on or about a person's head, with an array of ultrasound transducers mounted to the support structure. The method also involves selecting 1404, from an electronic memory, pre-recorded neurostimulation data developed to recreate a response by one or more of a sensing organ or organs, a vestibular system, and a memory of a subject. It is noted that the pre-recorded neurostimulation data can include neurostimulation data acquired from the subject or from person or persons other than the subject. The method further involves delivering 1406, using the array of ultrasound transducers and the pre-recorded neurostimulation data, transcranial stimulation to a specified region or regions of the subject's brain to recreate the response by one or more of the sensory organ or organs, the vestibular system, and the memory of the subject.

FIG. 14B illustrates methods which can be implemented using the apparatuses 1300a, 1300b shown in FIGS. 13A and 13B in accordance with various embodiments. The method shown in FIG. 14B include situating 1420 as support structure on or about a person's head, with an array of ultrasound transducers mounted to the support structure. The method also involves selecting 1422, from an electronic memory, pre-recorded olfactory neurostimulation data developed to recreate one or more predetermined odors. The method further involves delivering 1424, using the array of ultrasound transducers and the pre-recorded olfactory neurostimulation data, transcranial stimulation of the subject's olfactory system to recreate the one or more predetermined odors or variations of the one or more predetermined odors.

Figure 15A:
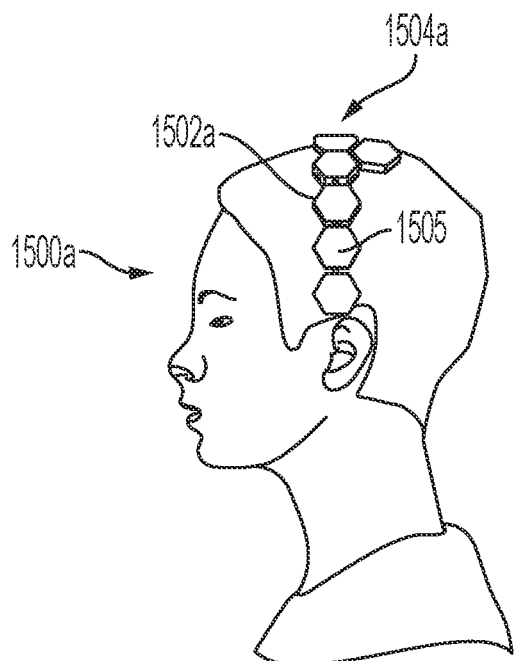
FIGS. 15A and 15B illustrate systems configured to deliver transcranial stimulation to a subject's brain in accordance with various embodiments.

FIG. 15A illustrates a system 1500a configured to deliver transcranial stimulation to a subject's brain in accordance with various embodiments. In the embodiment shown in FIG. 15A, the system 1500a is configured to be wearable by the subject and portable, which provides for real-time operation while the subject is ambulatory. The system 1500a includes a support structure 1502a configured for placement on a subject's head. In the representative embodiment shown in FIG. 15A, the support structure 1502a is implemented as a headband or other head-worn apparatus that extends generally from a location proximate the subject's left ear, across the left parietal ridge, over the top of the subject's head, across the right parietal ridge, and to location proximate the subject's right ear. Other configurations of the support structure 1502a are contemplated.

The support structure 1502a is configured to support an fUS transducer arrangement 1504a which, in the embodiment shown in FIG. 15A, includes an array of ultrasound transducers 1505. The fUS transducer arrangement 1504a can comprise an arrangement of interlocking ultrasound transducers 1505 mounted to the support structure 1502a. The arrangement of interlocking ultrasound transducers 1505 can comprise ultrasound transducers 1505 configured to be mechanically interlocking, communicatively (e.g., electrically and/or optically) interlocking, or both mechanically and communicatively interlocking with one another. The ultrasound transducers 1505 preferably have a compact design, and can have a size less than or equal to about 2 to 2.5 $cm^2$ and/or a volume less than or equal to about 2 $cm^3$. The ultrasound transducers 1505 are preferably mounted to the support structure 1502a such that the ultrasound transducers 1505 are positioned relative to a specified region or regions of the subject's brain of interest. For example, the ultrasound transducers 1505 can be mounted to the support structure 1502a relative to specific regions of the subject's olfactory system, including the olfactory cortex and the piriform cortex.

Figure 15B:
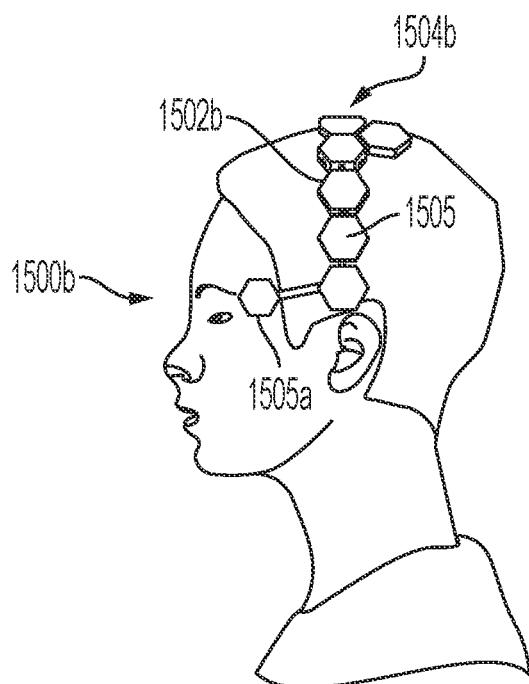

FIG. 15B illustrates a system 1500b configured to deliver transcranial stimulation to a subject's brain in accordance with various embodiments. The system 1500b shown in FIG. 15B can be configured to be the same as or similar to the system 1500a illustrated in FIG. 15A. The system 1500b includes a support structure 1502b configured to support an fUS transducer arrangement 1504b similar that shown in FIG. 15A. The support structure 1502b is configured to support an array of ultrasound transducers 1505 and additional ultrasound transducers 1505a positioned near the subject's temples and configured for delivering transcranial stimulation to a specified brain region or regions proximate the subject's temples. For example, the ultrasound transducers 1505 can be mounted to the support structure 1502b relative to specific regions of the subject's olfactory system, including the olfactory cortex and the piriform cortex, and the additional ultrasound transducers 1505a can be mounted to the support structure 1502b relative to the olfactory bulb located near the front of the brain in both cerebral hemispheres.

Figure 16:
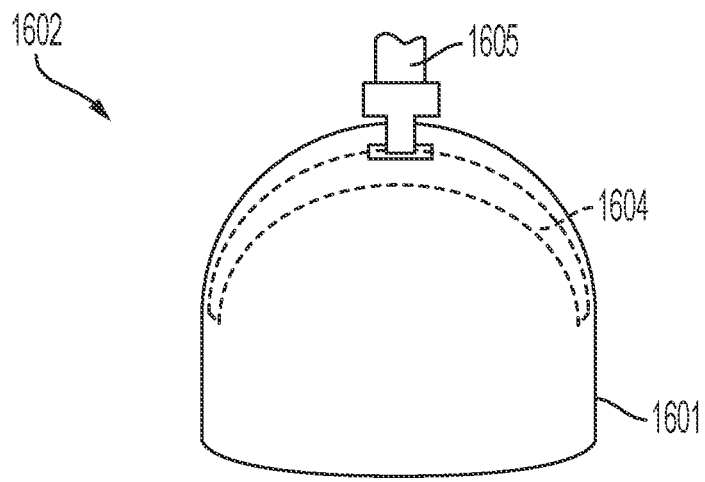
FIG. 16 illustrates a support structure configured to support a focused ultrasound transducer arrangement in accordance with various embodiments.

FIG. 16 illustrates a support structure 1602 configured to support an fUS transducer arrangement 1604 in accordance with various embodiments. The support structure 1602 shown in FIG. 16 includes a helmet structure 1602 within which an array of ultrasound transducers 1604 is mounted (individual ultrasound transducers not shown). The helmet structure 1602 is configured to be raised and lowered by an external mechanism relative to the subject's head when the subject is at a stationary (e.g., non-ambulatory) position. For example, the subject may be sitting in the chair of a test station and the helmet structure 1602 can be lowered and raised relative to the subject's head via a coupling member 1605 mechanically coupled to an external mechanism (e.g., a controllable manual or electromechanical lift mechanism).

Figure 17A:
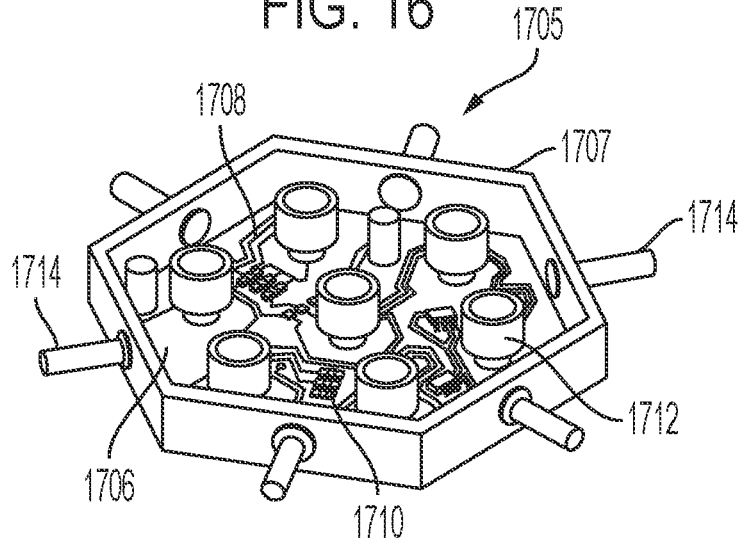
FIG. 17A illustrates a ultrasound transducer suitable for use in any of the ultrasound transducer arrangements disclosed herein in accordance with various embodiments.

FIG. 17A illustrates an ultrasound transducer 1705 suitable for use in any of the ultrasound transducer arrangements disclosed herein in accordance with various embodiments. The ultrasound transducer 1705 shown in FIG. 17A includes mechanical features configured to facilitate interlocking with one or more other ultrasound transducers 1705 of an ultrasound transducer arrangement (e.g., ultrasound transducer arrangement 1504a, 1504b shown in FIGS. 15A and 15B). The ultrasound transducer 1705 includes a chassis 1707 within which a PCB 1706 is disposed. One or more ultrasound transducer elements 1712 are positioned on or distributed about the PCB 1706. Each of the ultrasound transducer elements 1712 can be configured to deliver transcranial stimulation to a specified region or regions of a subject's brain. The ultrasound transducer elements 1712 can operate independently or cooperatively with respect to one another. The ultrasound transducer elements 1712 are communicatively connected to other electronic circuitry (e.g., electronic memory and/or controller) via traces 1708 disposed on the PCB 1706. The traces 1708 can include any combination of signal, control, and power lines. Various passive and active electronic components 1710 (see discussion of components 610 shown in FIG. 6A) can be disposed on the PCB 1706 and electrically connected to the ultrasound transducer elements 1712 via the traces 1708.

The chassis 1707 of the ultrasound transducer 1705 shown in FIG. 17A includes a multiplicity of interlocking members 1714. Typically, the chassis 1707 incorporates at least two of the interlocking members 1714, but may include more than two interlocking members 1714 (e.g., 3, 4, 5, or 17 interlocking members). Each of the interlocking members 1714 is configured to be received by a corresponding interlocking member of an adjacent ultrasound transducer 1705 (not shown, but see FIGS. 15A and 15B). For example, the interlocking members 1714 are shown as male connectors in FIG. 17A, which can be received by corresponding female interlocking members (e.g., female connectors) of an adjacent ultrasound transducer 1705. In some implementations, some of the interlocking members 1714 of the ultrasound transducer 1705 can be male connectors while others can be female connectors.

Figure 17B:
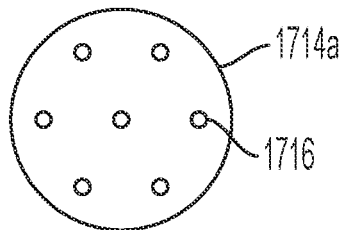
FIG. 17B is a front view of a connection interface of the interlocking members shown in FIG. 17A in accordance with various embodiments.

FIG. 17B is a front view of a connection interface 1714a of the interlocking members 1714 shown in FIG. 17A in accordance with various embodiments. The connection interface 1714a includes a number of connector elements (e.g., pins, ports, and/or receptacles) configured to provide electrical (and optionally optical) connectivity between the PCB 1706 of the ultrasound transducer 1705 and other electronic circuitry (e.g., PCBs 1706 of adjacent ultrasound transducers 1705, an electronic memory, and/or controller). The interlocking mechanical and electrical features of the ultrasound transducer 1705 provide for enhanced flexibility in terms of the number, configuration, and positioning of a multiplicity of ultrasound transducers 1705 that define a ultrasound transducer arrangement in accordance with various embodiments. For example, the interlocking mechanical and electrical features of the ultrasound transducers 1505 shown in FIGS. 15A and 15B provide for the addition of two extra ultrasound transducers 1505a positionable relative to a subject's left and right temples.

Figure 18:
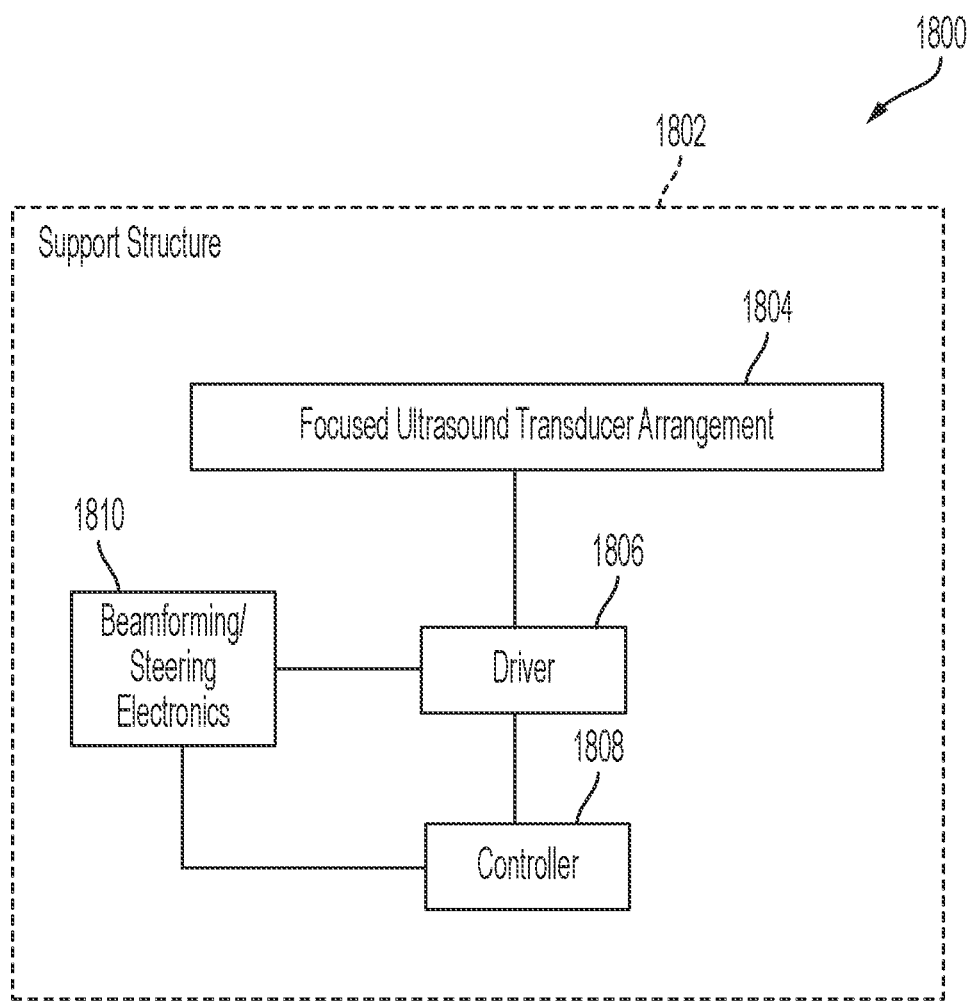
FIG. 18 illustrates a transcranial stimulation system comprising an focused ultrasound transducer arrangement in accordance with various embodiments.

FIG. 18 illustrates a transcranial stimulation system 1800 comprising an fUS transducer arrangement 1804 in accordance with various embodiments. The system 1800 includes a support structure 1802 configured for placement on or about a person's head. The fUS transducer arrangement 1804 is mounted to the support structure 1802. A driver 1806, a controller 1808, and optional beamforming/steering electronics 1810 are also mounted to, or supported by, the support structure 1802. The driver 1806 is operatively coupled to the fUS transducer arrangement 1804 and configured to drive and control each ultrasound transducer of the fUS transducer array in cooperation with the controller 1808. The controller 1808 is configured to adjust one or more parameters impacting transcranial stimulation delivered by the fUS transducer arrangement 1804 Beamforming/steering electronics 1810 can be operatively coupled to the controller 1808 and the driver 1806. The beamforming/steering electronics 1810 is configured to steer focusing of the fUS transducer arrangement 1804 towards specified region or regions (e.g., specified structures) of a subject's brain.

The fUS transducer arrangement 1804 is configured to deliver non-invasive (e.g., non-ionizing, non-destructive) neurostimulation to specified sites within a subject's brain. The fUS transducer arrangement 1804 can be configured for low-intensity fUS (LIFU). The fUS transducer arrangement 1804 delivers transcranial focused ultrasound (tFUS) having a higher spatial resolution, and capable of reaching deeper structures, when compared to conventional magnetic or electric non-invasive brain stimulation.

The fUS transducer arrangement 1804 can be configured to non-invasively deliver mechanical forces to structures deep within the brain in the form of an acoustic pressure wave, which can result in numerous bioeffects, both thermal and mechanical, depending on the specific pulsing regime. The acoustic waves can be focused to a particular location or region with a spatial resolution on the order of the wavelength of the driving frequency (e.g., approximately 3 mm at 0.5 MHz). As the focusing is achieved through constructive interference of the incident waves, a focal spot can be formed at a specified depth within the targeted brain tissue without affecting cells along the propagation path closer to the fUS transducer arrangement 1804.

Figure 19:
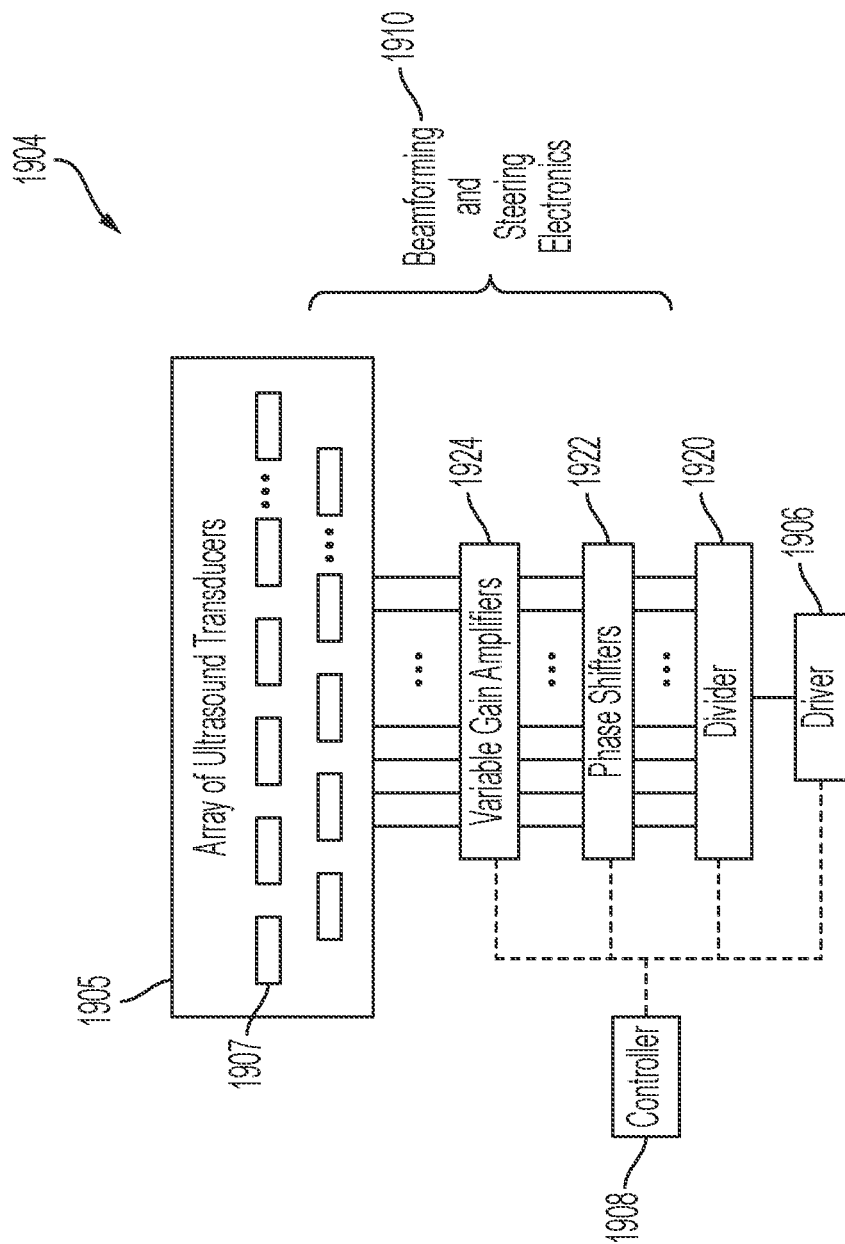
FIG. 19 illustrates a focused ultrasound transducer arrangement comprising an array of ultrasound transducers in accordance with various embodiments.

FIG. 19 illustrates a fUS transducer arrangement 1904 comprising an array of ultrasound transducers 1905 in accordance with various embodiments. The ultrasound transducer array 1905 includes a multiplicity of ultrasound transducer elements 1907. The ultrasound transducer elements 1907 can be arranged in any suitable pattern along a single axis (e.g. a one-dimensional (1-D) array) or multiple orthogonal axes (e.g., a 2-dimensional (2-D) array). FIG. 19 shows a driver 1906 operatively coupled to the array of ultrasound transducers 1905 via beamforming/steering electronics 1910. The fUS transducer arrangement 1904 can be implemented as a phased array of ultrasound transducer elements 1907. The beamforming/steering electronics 1910 includes a divider 1920 operatively coupled to the driver 1906. The divider 1920 can be a Wilkinson power divider, such as a compact multi-layer Wilkinson power divider. The divider 1920 is operatively coupled to a multiplicity of phase shifters 1922 and a multiplicity of variable gain amplifiers 1924. Each ultrasound transducer element 1907 is operatively coupled to a corresponding variable gain amplifier 1924 and phase shifter 1922.

A controller 1908 is operatively coupled to the driver 1906 and the beamforming/steering electronics 1910. The controller 1908 is configured to control the phase shifters 1922 and variable gain amplifiers 1924 to steer focusing of the ultrasound transducer elements 1907, such as by adjusting the phase shift of each of the phase shifters 1922. The beamforming/steering electronics 1910 can be configured to shape the spatial distribution of the pressure field amplitude in the volume of interest within a subject's brain. A challenge to accurately targeting a specified brain region concerns acoustic reflection, refraction, and distortion due to the inhomogeneity of skull bone. This challenge can be solved by time shifting each single ultrasound wave, according to the related skull bone acoustical properties, in order to permit all the waves to reach the target at the same time.

An acoustic wave can be defined by two fundamental parameters: the intensity, defined as the amplitude of the wave, and the instantaneous period (T), defined as the time needed to complete one single oscillation cycle, which is used to calculate the Acoustic frequency (Af). In addition to these two parameters, the stimulus duration (StimD) is the total duration of one single sonication. During the stimulus duration, two paradigms of sonication are used: continuous or pulsed. Some of these protocols resemble those used for non-invasive brain stimulation based on repetitive transcranial magnetic stimulation. The more popular protocol for neuromodulation is the pulsed paradigm.

For the pulsed paradigm, two additional periods are defined: the pulse duration (PD), which is the period of acoustic sonication from the starting point of oscillation to the ending point, before the pause and the pulse repetition period (PRP), which is the period between the starting point of two consecutive sonications, or, in other terms, the sum of the pulse duration (PD) and the pause between two consecutive sonications. This period is used to calculate the pulse repetition frequency (PRF). For the pulsed paradigm, the duty cycle (DC) is the fraction of the pulsed repetition period (PRP) covered by the pulse duration (PD). The cycles per pulse (c/p) are the number of cycles during a single pulse; instead, the number of pulses (Np) is the number of pulses throughout the stimulus duration. The sonication delivered during the stimulus duration period can be repeated, without pauses, for the continuous stimulation protocol. Intermittent protocols are characterized by pauses between the sonications, defined as inter stimulation intervals (ISIs). The intermittent protocol is the most used for fUS neurostimulation.

For safety reasons, the indexes that describe the thermal and biomechanical effects of the sonication have been defined. These parameters are related to the instantaneous intensity of stimulation and its instantaneous acoustic pressure. The two main mechanisms that can induce tissue damage are: local heating, which through proteins denaturation leads to cell death, and inertial cavitation. The latter is thought to be mediated by the collapse of gas bubbles due to the pressure exerted by ultrasonic field sufficiently strong to allow tissue damage. Both animal histological studies and human neuroimaging studies have shown that it is possible to neuromodulate brain circuits without inducing tissue damage. The thermal index (TI) is the ratio of total acoustic power to the acoustic power required to raise tissue temperature by 1° C. under defined assumptions. Finally, the non-thermal, mechanical bioeffect is described by the mechanical index (MI), which is directly proportional to the ultrasound beam's peak negative pressure and inversely proportional to the frequency of the beam.

The intensity, spatial-peak pulse-average (ISPPA) is the value of the pulse-average intensity at the point in the acoustic field where the pulse-average intensity is a maximum or is a local maximum within a specified region. The intensity, spatial-peak temporal-average (ISPTA) is the value of the temporal-average intensity at the point in the acoustic field where the temporal-average intensity is a maximum, or is a local maximum within a specified region. FDA guidelines define the safety threshold for diagnostic usage of fUS for adult cephalic ultrasound, which can be applied to neuromodulation. These parameters are Isspa≤190 W/cm$^2$, Ispta≤94 mW/cm$^2$ and a mechanical index ≤1.9.

Figure 20:
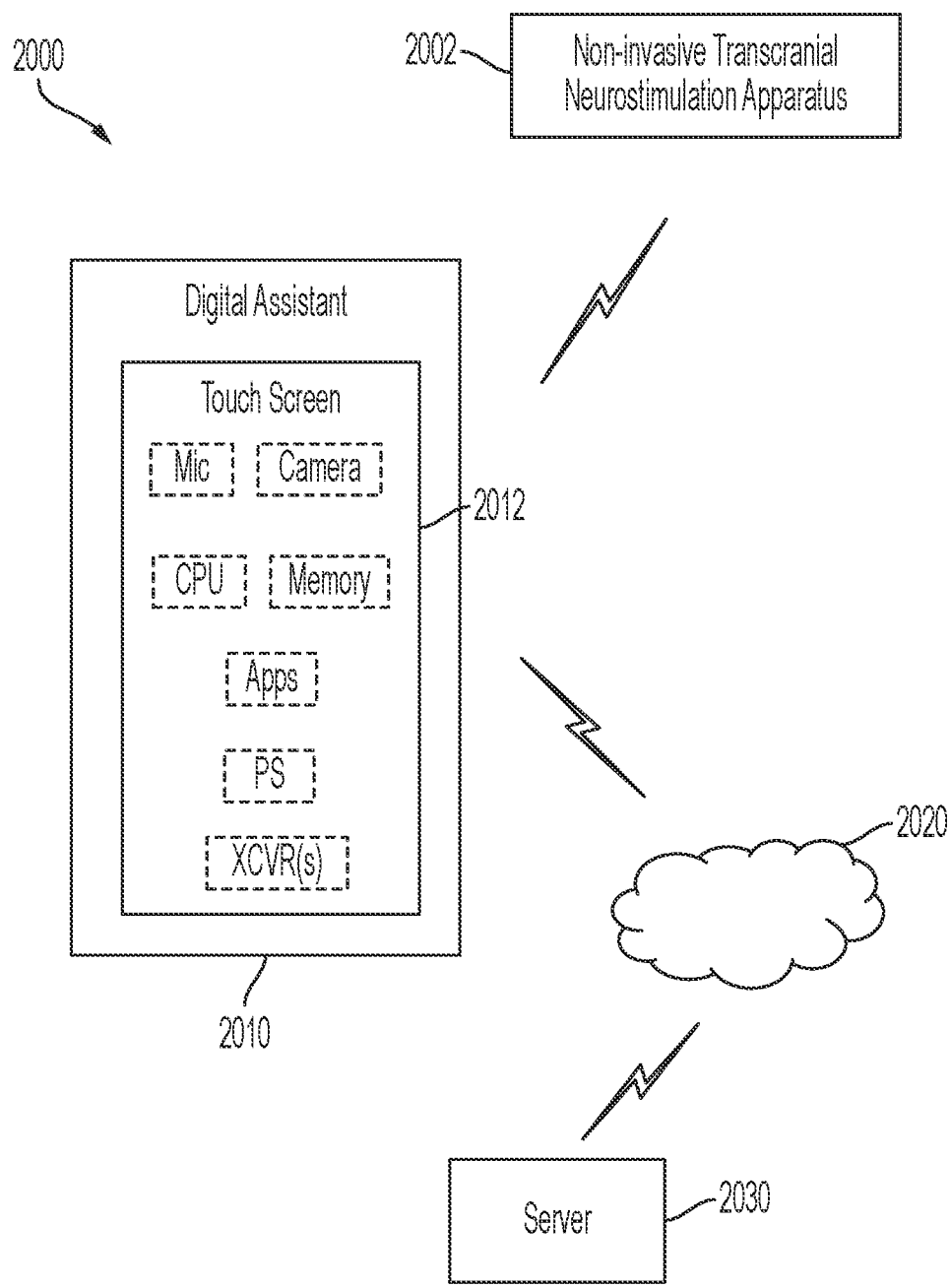
FIG. 20 illustrates a system configured to facilitate implementation of non-invasive transcranial neurostimulation in accordance with various embodiments.

FIG. 20 illustrates a system 2000 configured to facilitate implementation of non-invasive transcranial neurostimulation in accordance with various embodiments. The system 2000 shown in FIG. 20 includes a digital assistant device 2010 configured to communicatively couple to a non-invasive transcranial neurostimulation apparatus 2002 and a remote server 2030 via a network connection, such as the Internet 2020. The digital assistant device 2010 can be any mobile or stationary communication device, such as a smartphone, tablet, laptop or desktop PC, for example. The digital assistant device 2010 can include a touchscreen 2020 and a number of conventional components such as a microphone, camera, CPU, memory, power source, one or more radios or wireless transceivers (e.g., WiFi®, Bluetooth®, Zigbee®). The digital assistant device 2010 can also include one or more wired communication ports, such as USB or Ethernet ports. The digital assistant device 2010 includes one or more apps which can be stored in the memory and are executable by the CPU. At least one of the apps comprises executable instructions or program code that causes the CPU to cooperate with the non-invasive transcranial neurostimulation apparatus 2002 in accordance with any of the processes disclosed herein.

In some embodiments, the digital assistant device 2010 cooperates with the server 2032 (e.g., via the Internet) at least to acquire pre-recorded neurostimulation data (e.g., stored in cloud storage) comprising patterns of stimulation of a type or types previously described. A cloud processor can provide additional computing resources to facilitate delivery of transcranial stimulation to a specified region or regions of the subject's brain using the pre-recorded neurostimulation data. For example, the cloud processor can generate additional or variant neurorecording data, which can be transferred back to the digital assistance device 2010.

Figure 21:
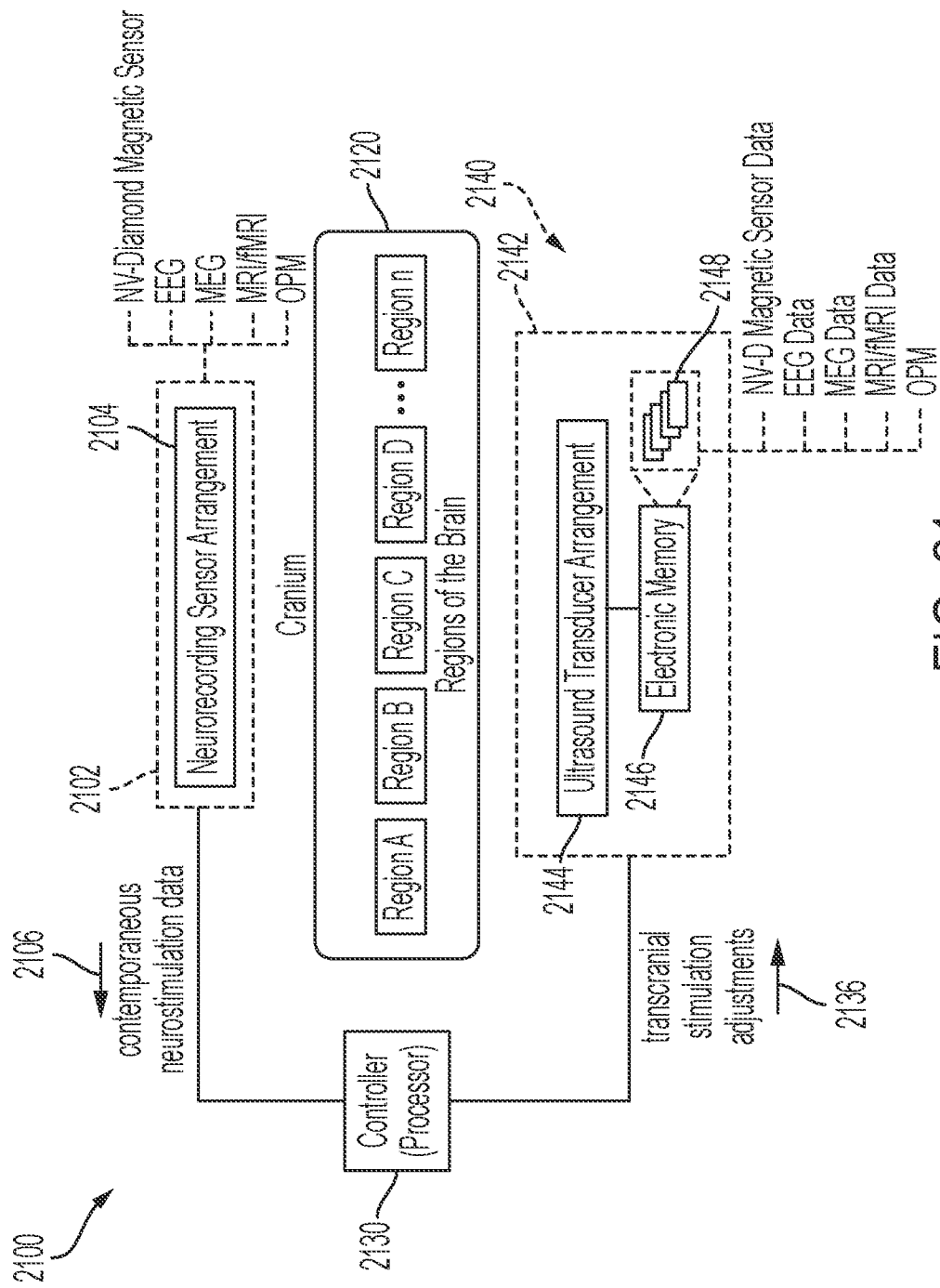
FIG. 21 illustrates a system configured to deliver transcranial stimulation to a specified region or regions of a subject's brain and to contemporaneously sense a response to the transcranial stimulation in accordance with various embodiments.

FIG. 21 illustrates a system 2100 configured to deliver transcranial stimulation to a specified region or regions of a subject's brain and to contemporaneously sense a response to the transcranial stimulation in accordance with various embodiments. The system 2100 includes a transcranial neurorecording sensor arrangement 2104 and a transcranial stimulation arrangement 2140, each of which is operatively coupled to a controller 2130. Components of the neurorecording sensor arrangement 2104 are mounted to a support structure 2102 configured for placement on or about a subject's head. The neurorecording sensor arrangement 2104 can have a configuration and functionality described previously with reference to the systems and methods shown in FIG. 1A through FIG. 12. Components of the transcranial stimulation arrangement 2140 are mounted to a support structure 2142 configured for placement on or about the subject's head. The transcranial stimulation arrangement 2140 can have a configuration and functionality described previously with reference to the systems and methods shown in FIG. 13A through FIG. 20. In some embodiments, components of the neurorecording sensor arrangement 2104 and the transcranial stimulation arrangement 2140 are mounted to a common support structure 2102 or 2142 configured for placement on or about the subject's head.

The transcranial stimulation arrangement 2140 includes an ultrasound transducer arrangement 2144 operatively coupled to an electronic memory 2146 and a controller (not shown, but see FIGS. 7-10A). The ultrasound transducer arrangement 2144 preferably includes an array of ultrasound transducers mounted to the support structure 2142. The transcranial stimulation arrangement 2140 is configured to deliver transcranial stimulation to a specified region or regions of the subject's brain 2120 using pre-recorded neurostimulation data stored in the electronic memory 2146. In addition or alternatively, the transcranial stimulation arrangement 2140 can be configured to deliver transcranial stimulation to a specified region or regions of the subject's brain 2120 using contemporaneous stimulation data acquired by the neurorecording sensor arrangement 2104. The contemporaneous stimulation data comprises neural activity data acquired by the neurorecording sensor arrangement 2104 during concurrent stimulation of the specified region or regions of the subject's brain 2120 via the transcranial stimulation arrangement 2140. The pre-recorded neurostimulation data comprises patterns 2148 of stimulation of the specified region or regions of the subject's brain or the brain of one or more persons other than the subject developed to recreate a response by one or more of the sensing organ or sensing organs, a vestibular system, and a memory of the subject.

The neurorecording sensor arrangement 2104 is configured to transcranially sense a response from a specified region or regions of the subject's brain initially cause by exposing the subject to stimuli and subsequently caused by delivery of transcranial stimulation by the transcranial stimulation arrangement 2140 using neurostimulation data recorded by the neurorecording sensor arrangement 2104. A wide variety of neurorecording sensor arrangements 2104 can be used in the context of an open-loop system or a closed-loop system in accordance with various embodiments. In some embodiments, the neurorecording sensor arrangement 2104 includes an array of magnetic sensors (e.g., NV-diamond magnetic sensors, OPM sensors) mounted to a support structure 2102/2142 and configured to sense local magnetic fields emanating from the specified region or regions of the subject's brain. In other embodiments, the neurorecording sensor arrangement 2104 includes an EEG sensor arrangement configured to acquire electroencephalogram data from the subject's brain for recording by the neurorecording sensor arrangement 2104.

In further embodiments, the neurorecording sensor arrangement 2104 includes a MEG sensor arrangement configured to acquire magnetoencephalography data from the subject's brain for recording by the neurorecording sensor arrangement 2104. In some embodiments, the neurorecording sensor arrangement 2104 includes an MM sensor arrangement configured to acquire magnetic resonance imaging data from the subject's brain for recording by the neurorecording sensor arrangement 2104. In other embodiments, the neurorecording sensor arrangement 2104 includes an fMRI sensor arrangement configured to acquire functional magnetic resonance imaging data (e.g., brain activity data detected by measuring small changes in cerebral blood flow) from the subject's brain for recording by the neurorecording sensor arrangement 2104.

Controlling operation of the array of ultrasound transducers by the controller 2130 can involve determining a difference between the contemporaneous neurostimulation data 2106 and the pre-recorded neurostimulation data, and comparing the difference to a predetermined threshold or a predetermined neural activity template. The controller 2130 is configured to produce transcranial stimulation adjustments 2136 in response to the difference exceeding or falling below the threshold or in response to a lack of correlation (e.g., >97%) relative to the predetermined neural activity template. In response to the transcranial stimulation adjustments 2136 generated by the controller 2130, the transcranial stimulation arrangement 2140 adjusts delivery of the transcranial stimulation. Adjusting delivery of the transcranial stimulation by the controller 2130 can involve one or more of adjusting a location or locations of the subject's brain subject to the transcranial stimulation, adjusting a spatiotemporal stimulation pattern of the transcranial stimulation, adjusting power of the transcranial stimulation, adjusting a frequency or a frequency range of the transcranial stimulation, adjusting a time duration or time parameter of the transcranial stimulation, adjusting a phase of the transcranial stimulation, and adjusting an amplitude of the transcranial stimulation. Adjustment of other parameters by the controller 2130 are contemplated.

According to some embodiments, a subject can be exposed to stimuli to stimulate one or more of a sensing organ or organs, a vestibular system, and a memory of the subject. The neurorecording sensor arrangement 2104 can be controlled by the controller 2130 to perform transcranial sensing of the specified region or regions of the subject's brain in response to the stimuli using any one or more of the sensor arrangements discussed above. The controller 2130, alone or in cooperation with another controller or processor, can be configured to operate on the data acquired from the neurorecording sensor arrangement 2104.

For example, the controller 2130, alone or in cooperation with another controller or processor, can be configured to operate on the data acquired from the neurorecording sensor arrangement 2104 by algorithmically determining, via machine learning, a spatiotemporal pattern needed to recreate the response (and/or a variation of the response) of one or more of the sensing organ or sensing organs, the vestibular method, and the memory of the subject stimulated by the stimuli. By way of further example, the controller 2130, alone or in cooperation with another controller or processor, can be configured to operate on the data acquired from the neurorecording sensor arrangement 2104 by algorithmically altering, via machine learning, the spatiotemporal pattern to produce an altered version of the spatiotemporal pattern. Various machine learning tools can be implemented by the controller 2130, alone or in cooperation with another controller or processor, including one or more of neural networks, convolutional neural networks (CNNs), and generative adversarial networks (GANs).

In some embodiments, the controller 2130, alone or in cooperation with another controller or processor, can be configured to algorithmically determine, via machine learning, one or both of the likelihood of stimulating the specified region or regions of the subject's brain in response to exposing the subject to the stimuli, and determine components of the stimuli that can be used as basis vectors to produce an altered spatiotemporal pattern that recreates an altered version of the response. Additionally, or alternatively, the controller 2130, alone or in cooperation with another controller or processor, can be configured to algorithmically predict, via machine learning, which particular region or regions of the subject's brain will be stimulated when stimulating the subject's brain to recreate an altered version of the response. Additionally, or alternatively, the controller 2130, alone or in cooperation with another controller or processor, can be configured to algorithmically determine, via machine learning, person-to-person variations of the transcranial stimulation based on physiology of a human head in order to infer properties for driving the array of ultrasound transducers needed to one or both of excite and suppress the particular region or regions of the subject's brain.

The spatiotemporal patterns needed to recreate the response (and/or a variation of the response) of one or more of the sensing organ or sensing organs, the vestibular method, and the memory of the subject stimulated by one of more stimuli are stored in the electronic memory 2146. The patterns 2148 can include neural activity data acquired from the same or a different type of transcranial sensing arrangement. For example, and as previously described, the patterns 2148 can include neural activity data acquired by an NV-diamond magnetic sensor arrangement. The patterns 2148 can include neural activity data acquired by an EEG sensor arrangement. The patterns 2148 can include neural activity acquired by and an MEG sensor arrangement. The patterns 2148 can include neural activity data acquired by an MRI or fMRI arrangement. The patterns 2148 can include neural activity data acquired by an OPM sensor arrangement. It is understood that the patterns 2148 can include neural activity data acquired from any one or any combination of these and other transcranial sensing arrangements.

Figure 22:
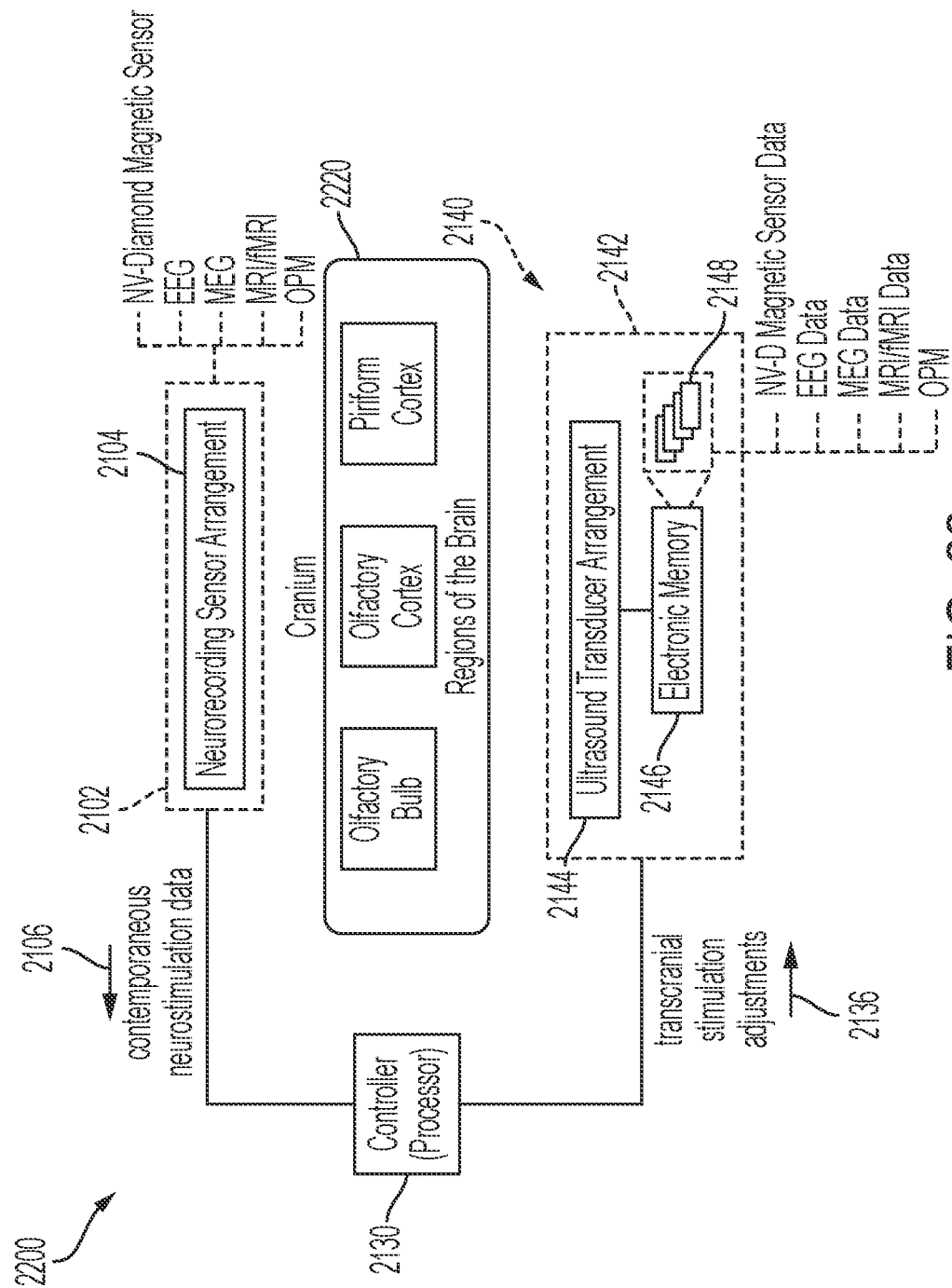
FIG. 22 illustrates a system configured to deliver transcranial stimulation to an olfactory system of a subject's brain and to contemporaneously sense a response to the transcranial stimulation in accordance with various embodiments.

FIG. 22 illustrates a system 2200 configured to deliver transcranial stimulation to an olfactory system 2220 of a subject's brain and to contemporaneously sense a response to the transcranial stimulation in accordance with various embodiments. The system 2200 is a variant of the system 2100 shown in FIG. 21. In the embodiment shown in FIG. 22, the transcranial stimulation arrangement 2140 includes an ultrasound transducer arrangement 2144 comprising an array of ultrasound transducers which, under the control of the controller 2130, delivers transcranial stimulation to the subject's olfactory system 2220. As previously discussed, the transcranial stimulation arrangement 2140 can use one or both of pre-recorded and contemporaneous olfactory stimulation data acquired from the neurorecording sensor arrangement 2104.

The transcranial stimulation arrangement 2140 shown in FIG. 22 is configured to deliver transcranial stimulation to one or more of the subject's olfactory cortex, piriform cortex, and olfactory bulb to recreate a sense of one or more of predetermined odors or variations of one or more of the predetermined odors. The transcranial neurorecording sensor arrangement 2104 is configured to transcranially sense and record local magnetic fields emanating from one or more of the subject's olfactory cortex, piriform cortex, and olfactory bulb caused by delivery of the transcranial stimulation.

Figure 23:
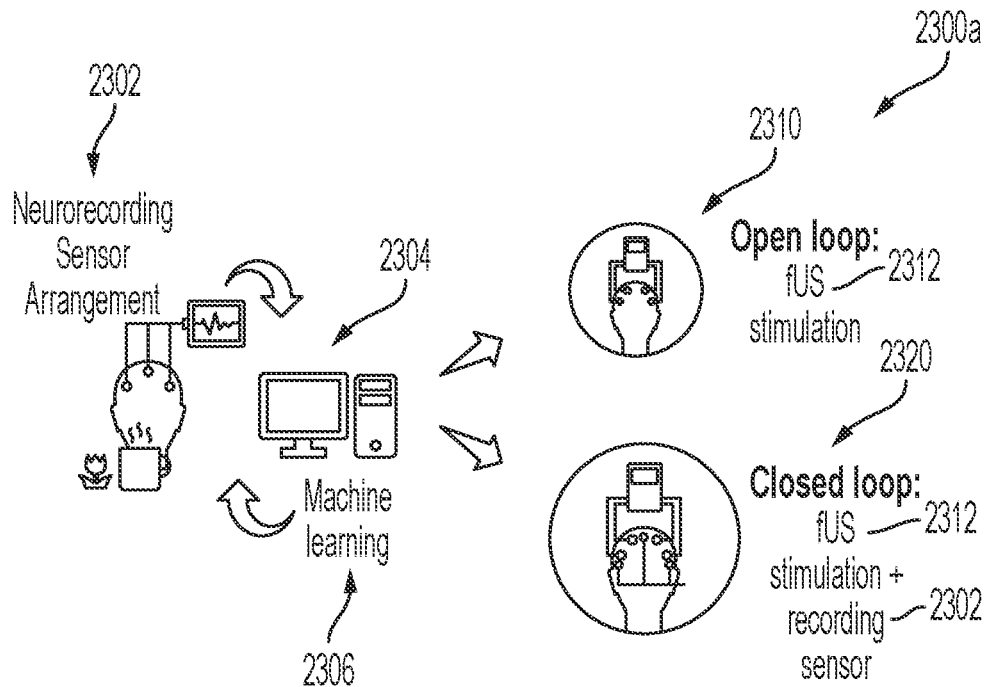
FIG. 23 illustrates a system configured to deliver transcranial stimulation to an olfactory system of a subject's brain and to contemporaneously sense a response to the transcranial stimulation in accordance with various embodiments.
Figure 24:
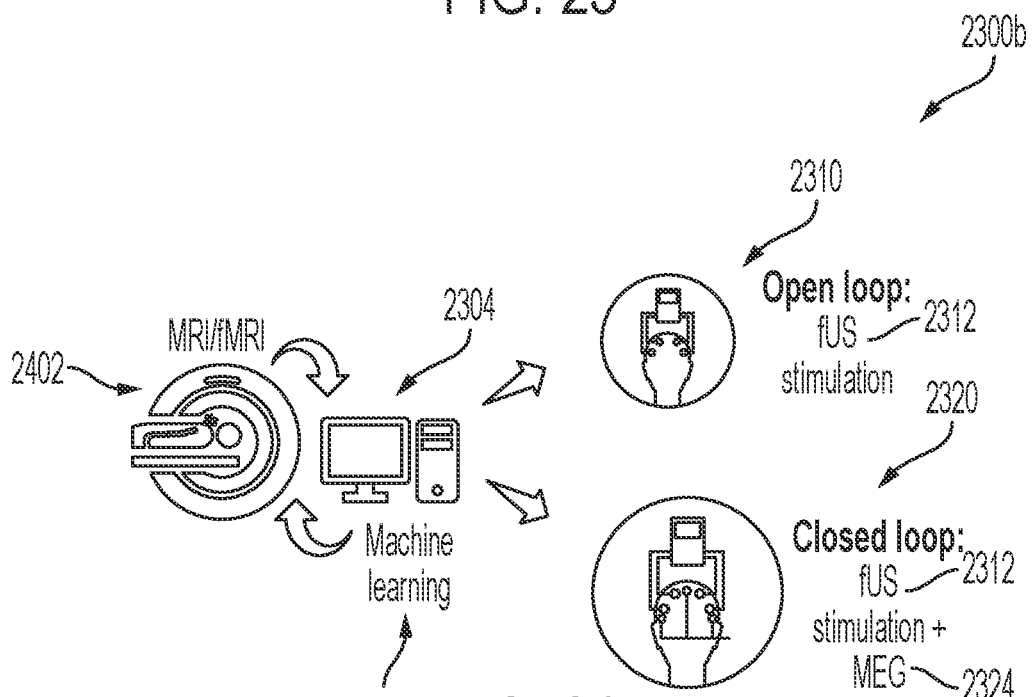
FIG. 24 illustrates a system configured to deliver transcranial stimulation to an olfactory system of a subject's brain and to contemporaneously sense a response to the transcranial stimulation in accordance with various embodiments.

FIGS. 23 and 24 illustrate a system 2300a, 2300b configured to transcranially record neural activity, process recorded neural activity data using processor-implemented algorithms and/or machine learning, and transcranially stimulate a subject's brain using the processed recorded neural activity data in accordance with various embodiments. The system 2300a is configured as a relatively fast, but lower fidelity, system. The system 2300b is configured as a relatively slow, but higher fidelity, system. Each of the systems 2300a, 2300b can be configured to provide open-loop transcranial stimulation of a subject's brain or closed-loop transcranial stimulation/neurorecording of a subject's brain.

Many of the components of systems 2300a and 2300b are largely the same or similar, and largely have the same or similar functionality. However, system 2300a includes a faster, but lower fidelity, neurorecording sensor arrangement 2302 in the form of an array of magnetic sensors (e.g., NV-diamond or OPM sensors) and/or an EEG sensor arrangement. In the closed-loop implementation 2320 of system 2300a, the neurorecording sensor 2302 can be the same sensor as that used in the neurorecording sensor arrangement 2302.

The system 2300b includes a slower, but higher fidelity, neurorecording sensor arrangement 2402 in the form of an MRI sensor or an fMRI sensor. In the closed-loop implementation 2320 of system 2300b, the neurorecording sensor 2324 is typically a different sensor from that used in the neurorecording sensor arrangement 2402, such as an MEG sensor.

The systems 2300a, 2300b can be configured to transcranially record neural activity in one or more of a sensing organ or organs, a vestibular system, and a memory of the subject's brain while exposing the subject to stimuli. In addition, the systems 2300a, 2300b can be configured to transcranially stimulate, using previously recorded neural activity data, one or more of a sensing organ or organs, a vestibular system, and a memory of the subject. The transcranial stimulation can be used to recreate a response (and/or a variation of the response) of one or more of the sensing organ or sensing organs, the vestibular method, and the memory of the subject stimulated by the stimuli during the transcranial neurorecording process. The transcranial stimulation can also be used to convey and/or elicit abstract data (e.g., an order from a commanding officer, a memory) without use or stimulation of the subject's vision/ocular system.

The systems 2300a, 2300b include a neurorecording sensor arrangement 2302, 2402 of a type previously described. During a training phase, the subject is exposed to stimuli to stimulate one or more of a sensing organ or organs, a vestibular system, and a memory of the subject. For example, the subject can be exposed to one or more predetermined odors to stimulate the olfactory system of the subject. While the subject is exposed to the stimuli, the neurorecording sensor arrangement 2302, 2402 is configured to record neurostimulation data representative of patterns of stimulation of the specified region or regions of the subject's brain in response to the stimuli. For example, the neurorecording sensor arrangement 2302, 2402 can be configured to record neurostimulation data representative of patterns of stimulation of the subject's olfactory system including one or more of the subject's olfactory cortex, piriform cortex, and olfactory bulb in response to the subject smelling one or more predetermined odors.

A controller 2304 (shown as a computer system including a desktop PC comprising one or more processors operatively coupled to an optional display) is configured to operate on the data produced by the neurorecording sensor arrangement 2302, 2402 by algorithmically determining, via machine learning, a spatiotemporal pattern needed to recreate the response (and/or a variation of the response) of one or more of the sensing organ or sensing organs, the vestibular method, and the memory of the subject stimulated by the stimuli. As previously discussed, various machine learning tools can be implemented by the controller 2304, alone or in cooperation with another controller or processor, including one or more of neural networks, convolutional neural networks (CNNs), and generative adversarial networks (GANs). The controller 2304 generates a multiplicity of spatiotemporal patterns associated with the subject's response to a corresponding multiplicity of stimuli. The spatiotemporal patterns are stored in an electronic memory of, or operatively coupled to, the controller 2304.

In an open-loop implementation 2310 and a closed-loop implementation 2320 of systems 2300a and 2300b, one or more selected spatiotemporal patterns stored in the memory of the controller 2304 are communicated to a transcranial stimulation arrangement 2312 (e.g., a focused ultrasound array). The transcranial stimulation arrangement 2312 delivers focused ultrasound to a specified region or regions of the brain to recreate a response (and/or a variation of the response) of one or more of the sensing organ or sensing organs, the vestibular method, and the memory of the subject stimulated by the stimuli associated with the one or more selected spatiotemporal patterns. In addition, or alternatively, the transcranial stimulation arrangement 2312 can deliver focused ultrasound to a specified region or regions of the brain to convey and/or illicit abstract data.

In the closed-loop implementation 2320, the neurorecording sensor arrangement 2302, 2324 is used to transcranially sense contemporaneous stimulation data and generate neural activity data during concurrent stimulation of the specified region or regions of the subject's brain via the transcranial stimulation arrangement 2322. The contemporaneous stimulation data acquired or produced by the neurorecording sensor arrangement 2302, 2324 can be used by the controller 2304 refine the spatiotemporal patterns needed to recreate the response of one or more of the sensing organ or sensing organs, the vestibular method, and the memory of the subject stimulated by the stimuli. This contemporaneous stimulation data can also be used to alter the spatiotemporal patterns to recreate a variation of the response of one or more of the sensing organ or sensing organs, the vestibular method, and the memory of the subject stimulated by the stimuli.

For example, the controller 2304 can be configured to produce a spatiotemporal pattern representative of the subject's olfactory response to a particular perfume. The controller 2304 can be further configured to produce a variant spatiotemporal pattern to recreate a variation of the subject's olfactory response to the particular perfume. As such, the subject believes that he or she is smelling a variation of the particular perfume, which can facilitate the rapid development of new and pleasing perfumes at a substantially reduces cost. Machine learning can be used to tailor the specific stimulation protocols for each subject, based on their physiology and prior training experiences. The closed-loop implementation 2320 improves stimulation in real-time by ensuring that the subject's olfactory system is activated in the same manner as if the subject user had a conventional olfactory experience by directly smelling the perfume.

The systems 2300a, 2300b illustrated in FIGS. 23 and 24 advantageously provide for a completely non-invasive (e.g., non-ionizing, non-destructive) high-resolution stimulation technique accompanied by imaging (varying fidelity) to create closed-loop transcranial recording of neural activity from specified sites of a subject's brain, recreation of a response by one or more of a sensing organ or sensing organs, a vestibular system, and a memory of the subject via transcranial focused ultrasound, and a means to convey abstract data. The systems 2300a, 2300b illustrated in FIGS. 23 and 24 advantageously provide for an enhanced HMI (Human Machine Interface), faster skill training, selective memory recollection, enhanced realistic experience, recreating personalized sensory (e.g., olfactory) experience, and 'recording' and 'recreating' sensed experiences without the need of physical stimuli (e.g., recreating smells without the need of chemicals). The systems 2300a, 2300b illustrated in FIGS. 23 and 24 advantageously provide for integrated headgear to augment a virtual reality experience with recreated sensor experience.

Figure 25A:
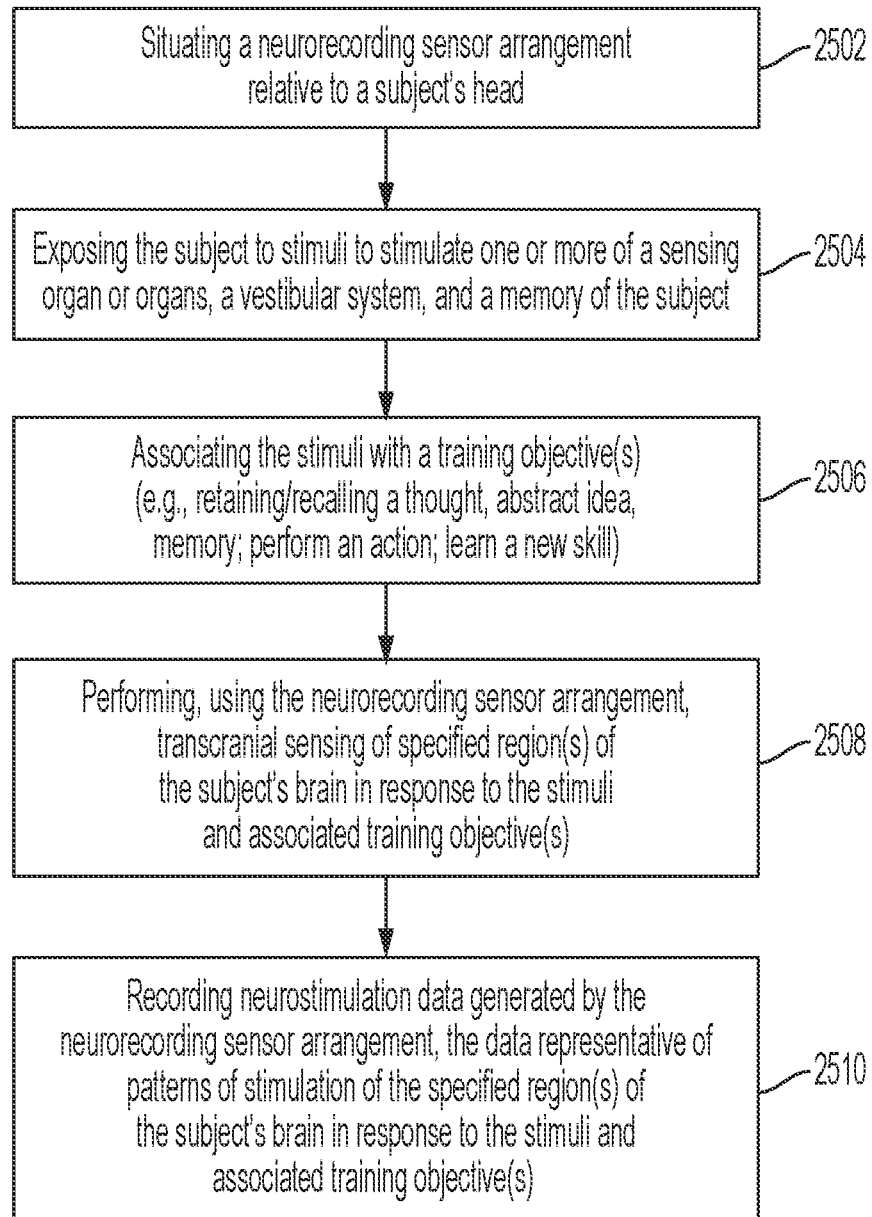
FIGS. 25A and 25B illustrate methods that can be implemented by the systems shown in FIGS. 23 and 24 in accordance with various embodiments.

FIG. 25A illustrates a method that can be implemented by the systems 2300a, 2300b shown in FIGS. 23 and 24 in accordance with various embodiments. The method shown in FIG. 25A involves situating 2502 a neurorecording sensor arrangement relative to a subject's head. The method involves exposing 2504 the subject to stimuli to stimulate one or more of a sensing organ or organs, of the stimulus system, and a memory of the subject. The method also involves associating 2506 the stimuli with a training objective or objectives, such as retaining/recalling a thought, an abstract idea, and memory, performing an action, or learning a new skill. The method further involves performing 2508, using the neurorecording sensor arrangement, transcranial sensing of specified region or regions of the subject's brain in response to the stimuli and associated training objective(s). The method also involves recording 2510 neurostimulation data generated by the neurorecording sensor arrangement. The recorded data is representative of patterns of stimulation of the specified region or regions of the subject's brain in response to the stimuli and associated training objective(s).

Figure 25B:
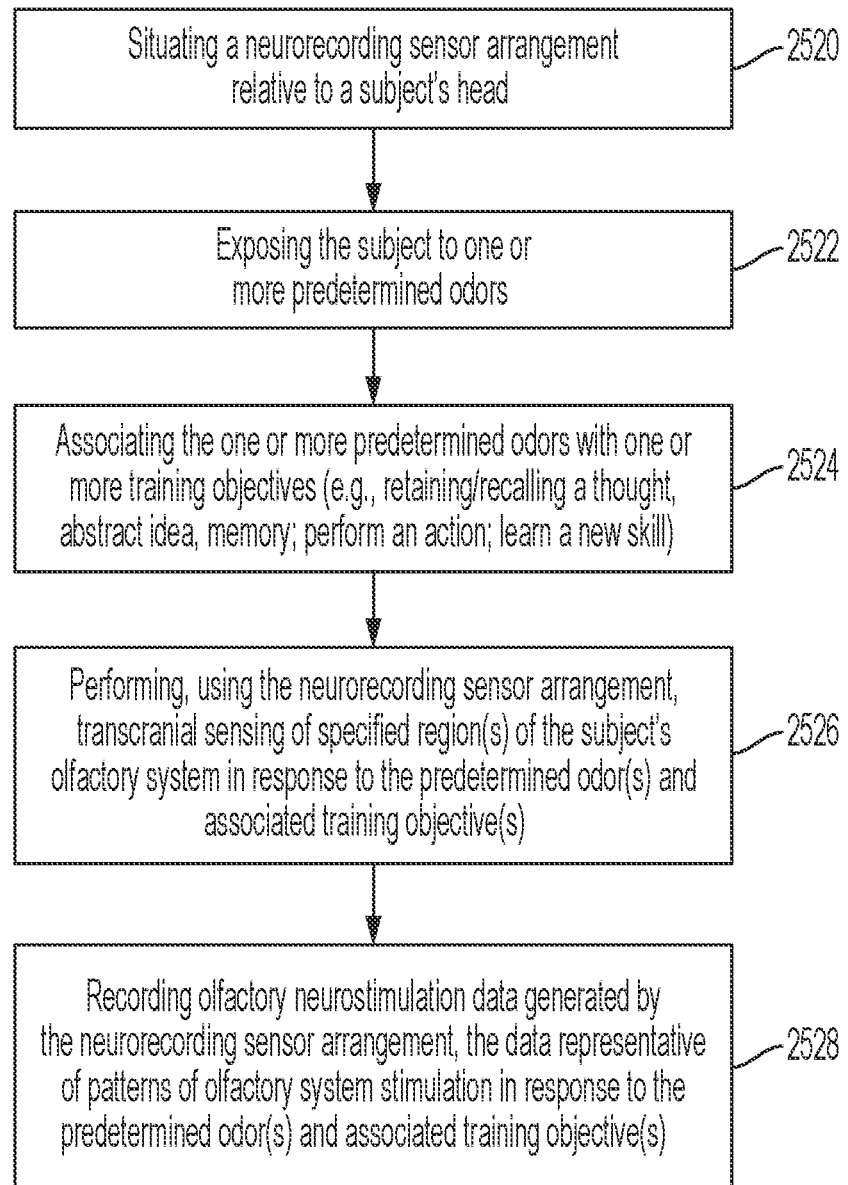

FIG. 25B illustrates a method that can be implemented by the systems 2300a, 2300b shown in FIGS. 23 and 24 in accordance with various embodiments. The method shown in FIG. 25B involves situating 250 a neurorecording sensor arrangement relative to a subject's head. The method involves exposing 2522 the subject to one or more predetermined odors. The method also involves associating 2524 the one or more predetermined odors with one or more training objectives (e.g., see examples above). The method further involves performing 2526, using the neurorecording sensor arrangement, transcranial sensing of a specified region or regions of the subject's olfactory system in response to the predetermined odor(s) and associated training objective(s). The method also involves recording 2528 olfactory neurostimulation data generated by the neurorecording sensor arrangement. The recorded data is representative of patterns of olfactory system stimulation in response to the predetermined odor(s) and associated training objective(s).

Figure 26A:
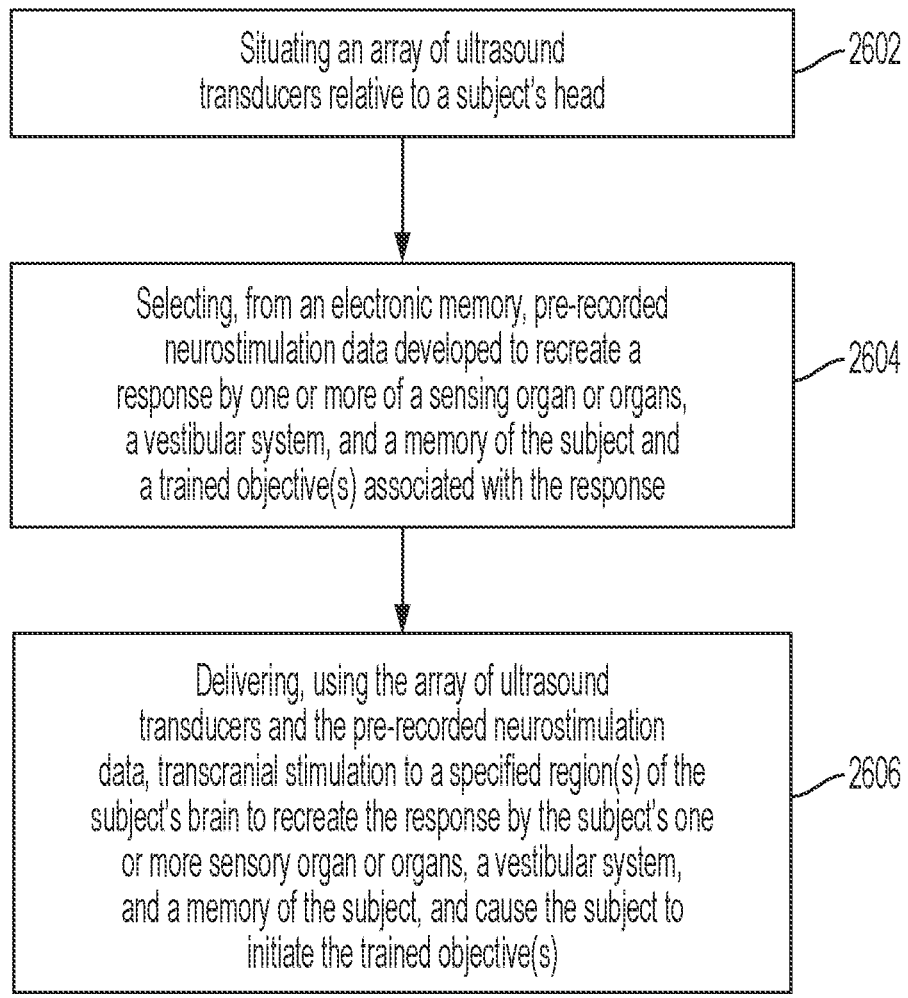
FIGS. 26A and 26B illustrate methods that can be implemented by the systems shown in FIGS. 23 and 24 in accordance with various embodiments.

FIG. 26A illustrates a method that can be implemented by the systems 2300a, 2300b shown in FIGS. 23 and 24 in accordance with various embodiments. The method shown in FIG. 26A involves situating 2602 an array of ultrasound transducers relative to a subject's head. The method also involves selecting 2604, from an electronic memory, pre-recorded neurostimulation data developed to recreate a response by one or more of a sensing organ or organs, a vestibular system, and a memory of the subject and a trained objective or objectives associated with the response. The method further involves delivering 2606, using the array of ultrasound transducers and the pre-recorded neurostimulation data, transcranial stimulation to a specified region or regions of the subject's brain to recreate the response by the subject's one or more sensing organ or organs, vestibular system, and memory of the subject.

Figure 26B:
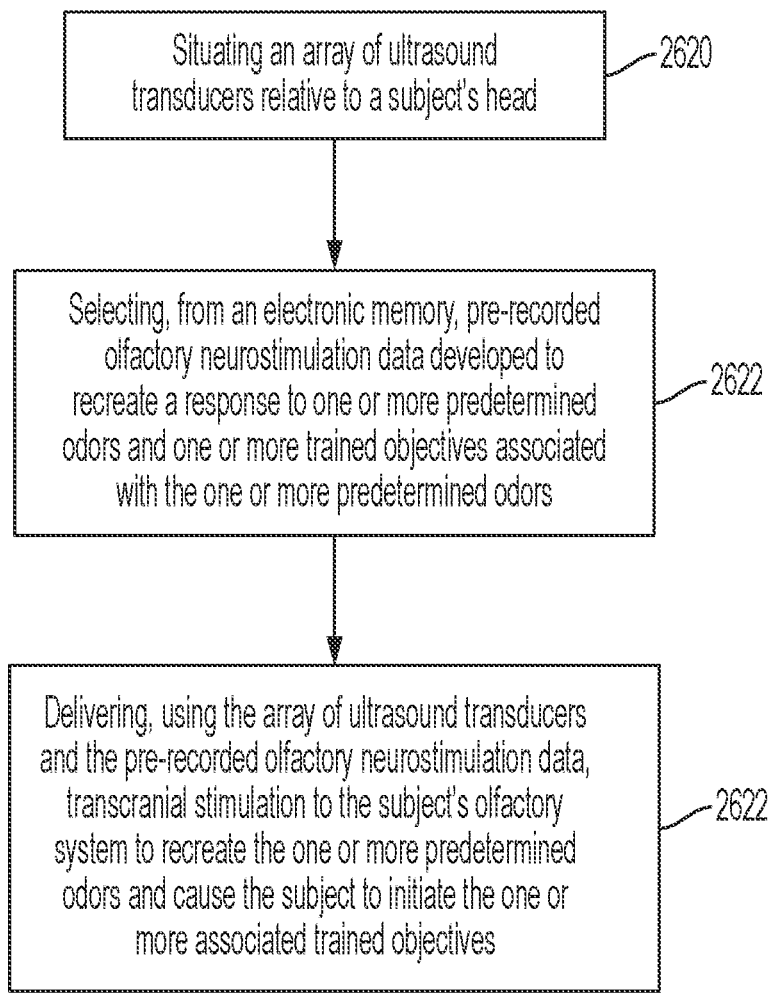

FIG. 26B illustrates a method that can be implemented by the systems 2300a, 2300b shown in FIGS. 23 and 24 in accordance with various embodiments. The method shown in FIG. 26B involves situating 2620 an array of ultrasound transducers relative to a subject's head. The method also involves selecting 2622, from an electronic memory, pre-recorded olfactory neurostimulation data developed to recreate a response to one or more predetermined odors and one or more trained objectives associated with the one or more predetermined odors. The method further involves delivering 2622, using the array of ultrasound transducers and the pre-recorded olfactory neurostimulation data, transcranial stimulation to the subject's olfactory system to recreate the one or more predetermined odors and cause the subject to initiate the one or more associated trained objectives.

It is understood that the controllers and processors shown in the figures can include or be operatively coupled to a main memory and a non-volatile memory. The controllers and processors can be implemented as one or more of a multi-core processor, a digital signal processor (DSP), a microprocessor, a programmable controller, a general-purpose computer, a special-purpose computer, a hardware controller, a software controller, a combined hardware and software device, such as a programmable logic controller, and a programmable logic device (e.g., FPGA, ASIC). The controllers and processors can include or be operatively coupled to main memory, such as RAM (e.g., DRAM, SRAM). The controllers and processors can include or be operatively coupled to non-volatile memory, such as ROM, EPROM, EEPROM or flash memory.

Although reference is made herein to the accompanying set of drawings that form part of this disclosure, one of at least ordinary skill in the art will appreciate that various adaptations and modifications of the embodiments described herein are within, or do not depart from, the scope of this disclosure. For example, aspects of the embodiments described herein may be combined in a variety of ways with each other. Therefore, it is to be understood that, within the scope of the appended claims, the claimed invention may be practiced other than as explicitly described herein.

All references and publications cited herein are expressly incorporated herein by reference in their entirety into this disclosure, except to the extent they may directly contradict this disclosure. Unless otherwise indicated, all numbers expressing feature sizes, amounts, and physical properties used in the specification and claims may be understood as being modified either by the term "exactly" or "about." Accordingly, unless indicated to the contrary, the numerical parameters set forth in the foregoing specification and attached claims are approximations that can vary depending upon the desired properties sought to be obtained by those skilled in the art utilizing the teachings disclosed herein or, for example, within typical ranges of experimental error.

The recitation of numerical ranges by endpoints includes all numbers subsumed within that range (e.g. 1 to 5 includes 1, 1.5, 2, 2.75, 3, 3.80, 4, and 5) and any range within that range. Herein, the terms "up to" or "no greater than" a number (e.g., up to 50) includes the number (e.g., 50), and the term "no less than" a number (e.g., no less than 5) includes the number (e.g., 5).

The terms "coupled" or "connected" refer to elements being attached to each other either directly (in direct contact with each other) or indirectly (having one or more elements between and attaching the two elements). Either term may be modified by "operatively" and "operably," which may be used interchangeably, to describe that the coupling or connection is configured to allow the components to interact to carry out at least some functionality (for example, a radio chip may be operably coupled to an antenna element to provide a radio frequency electric signal for wireless communication).

Terms related to orientation, such as "top," "bottom," "side," and "end," are used to describe relative positions of components and are not meant to limit the orientation of the embodiments contemplated. For example, an embodiment described as having a "top" and "bottom" also encompasses embodiments thereof rotated in various directions unless the content clearly dictates otherwise.

Reference to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout are not necessarily referring to the same embodiment of the disclosure. Furthermore, the particular features, configurations, compositions, or characteristics may be combined in any suitable manner in one or more embodiments.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the disclosure.

As used in this specification and the appended claims, the singular forms "a," "an," and "the" encompass embodiments having plural referents, unless the content clearly dictates otherwise. As used in this specification and the appended claims, the term "or" is generally employed in its sense including "and/or" unless the content clearly dictates otherwise.

As used herein, "have," "having," "include," "including," "comprise," "comprising" or the like are used in their open-ended sense, and generally mean "including, but not limited to." It will be understood that "consisting essentially of" "consisting of," and the like are subsumed in "comprising," and the like. The term "and/or" means one or all of the listed elements or a combination of at least two of the listed elements.

The phrases "at least one of," "comprises at least one of," and "one or more of" followed by a list refers to any one of the items in the list and any combination of two or more items in the list.

What is claimed is:

1. A system, comprising:
    an electronic memory configured to store pre-recorded neurostimulation data comprising patterns of stimulation of a specified region of a subject's brain developed to recreate a response by one or more of a sensing organ or sensing organs of the subject, the pre-recorded neurostimulation data acquired using an array of magnetic sensors mechanically and communicatively interlocking with one another and configured for transcranial sensing of local magnetic fields emanating from the specified region of the subject's brain caused by stimulating one or more of the sensing organ or sensing organs of the subject;
    a focused ultrasound transducer arrangement operably coupled to the electronic memory and comprising an array of ultrasound transducers mechanically and communicatively interlocking with one another, the focused ultrasound transducer arrangement configured to deliver transcranial stimulation to the specified region of the subject's brain using the pre-recorded neurostimulation data to recreate the response by one or more of the sensing organ or sensing organs of the subject; and
    a support structure configured for placement on or about the subject's head, the support structure configured to support at least the array of interlocking magnetic sensors and the array of interlocking ultrasound transducers, wherein:
    the interlocking ultrasound transducers are configured with interlocking mechanical and electrical features that facilitate addition of one or more additional ultrasound transducers to the support structure; and
    the interlocking magnetic sensors are configured with interlocking mechanical and electrical/optical features that facilitate addition of one or more additional magnetic sensors to the support structure.

2. The system of claim 1, wherein the array of magnetic sensors comprises nitrogen-vacancy (NV) diamond magnetic sensors.

3. The system of claim 1, wherein the system is configured to be wearable and portable.

4. The system of claim 1, wherein the array of magnetic sensors comprises optically pumped magnetic (OPM) sensors.

5. The system of claim 1, comprising:
    a driver operably coupled to the array of ultrasound transducers; and
    a controller operably coupled to the driver and the focused ultrasound transducer arrangement, the controller configured to adjust one or more parameters impacting the transcranial stimulation.

6. The system of claim 5, comprising:
    beamforming circuitry operatively coupled to the driver and the controller;
    wherein the controller is configured to control the beamforming circuitry to steer focusing of the focused ultrasound transducer arrangement.

7. The system of claim 1, comprising a communication interface configured to facilitate one or both of wired and wireless communication between the system and an external electronic system or device.

8. The system of claim 7, wherein the external electronic system or device comprises a tablet, a laptop, a smartphone or a personal digital assistant configured to execute an app that facilitates one or more of:
    selection of specified stored pre-recorded neurostimulation data to evoke the response by one or more of the sensing organ or sensing organs of the subject;
    selection of specified stored pre-recorded neurostimulation data to evoke a variation of the response by one or more of the sensing organ or sensing organs of the subject; and
    communication of one or both of the subject's response and variation of the response.

9. The system of claim 1, wherein the pre-recorded neurostimulation data stored in the electronic memory comprises spatiotemporal neural activity patterns.

10. The system of claim 1, wherein:
    the pre-recorded neurostimulation data stored in the electronic memory is representative of patterns of stimulation of the subject's olfactory system including one or more of the subject's olfactory cortex, piriform cortex, and olfactory bulb, the pre-recorded neurostimulation data associated with one or more predetermined odors; and
    the focused ultrasound transducer arrangement is configured to deliver transcranial stimulation to one or more of the subject's olfactory cortex, piriform cortex, and olfactory bulb to recreate a sense of one or more of the predetermined odors or variations of the one or more of the predetermined odors.

11. The system of claim 1, wherein:
    the pre-recorded neurostimulation data stored in the electronic memory is representative of patterns of stimulation of one or more of the subject's vision, hearing, touch, and taste organs; and
    the focused ultrasound transducer arrangement is configured to deliver transcranial stimulation to one or more of a vision, hearing, touch, and taste sense organ-processing region or regions of the subject's brain to recreate a sense of one or more of a vision, hearing, touch, and taste response.

12. A method, comprising:
    situating a support structure on or about a subject's head, an array of ultrasound transducers mounted to the support structure such that the ultrasound transducers are mechanically and communicatively interlocking with one another;
    selecting, from an electronic memory, pre-recorded neurostimulation data developed to recreate a response by one or more of a sensing organ or organs of the subject, the pre-recorded neurostimulation data acquired using an array of mechanically and communicatively interlocking magnetic sensors mounted to the support structure and configured for transcranial sensing of local magnetic fields emanating from a specified region of the subject's brain caused by stimulating one or more of the sensing organ or sensing organs of the subject; and delivering, using the array of ultrasound transducers and the pre-recorded neurostimulation data, transcranial stimulation to a specified region or regions of the subject's brain to recreate the response by one or more of the sensing organ or organs of the subject, wherein:

the interlocking ultrasound transducers are configured with interlocking mechanical and electrical features that facilitate addition of one or more additional ultrasound transducers to the support structure; and the interlocking magnetic sensors are configured with interlocking mechanical and electrical/optical features that facilitate addition of one or more additional magnetic sensors to the support structure.

13. The method of claim 12, comprising performing the method by the subject when ambulatory.

14. The method of claim 12, wherein the array of magnetic sensors comprises nitrogen-vacancy (NV) diamond magnetic sensors or optically pumped magnetic (OPM) sensors.

15. The method of claim 12, comprising:
driving the array of ultrasound transducers using a driver; and
adjusting one of more parameters impacting the transcranial stimulation by a controller operatively coupled to the driver.

16. The method of claim 15, comprising controlling, by the controller, beamforming circuitry to steer focusing of the focused ultrasound transducer.

17. The method of claim 12, comprising:
controlling one or both of the array of ultrasound transducers and the electronic memory by a controller, and
facilitating, via a communication interface, one or both of wired and wireless communication between the controller and an external electronic system or device.

18. The method of claim 17, wherein the external electronic system or device comprises a tablet, a laptop, a smartphone or a personal digital assistant configured to execute an app that facilitates one or more of:
selecting specified stored pre-recorded neurostimulation data to evoke the response by one or more of the sensing organ or sensing organs of the subject;
selecting specified stored pre-recorded neurostimulation data to evoke a variation of the response by one or more of the sensing organ or sensing organs of the subject; and
communication of one or both of the subject's response and variation of the response.

19. The method of claim 12, wherein the pre-recorded neurostimulation data stored in the electronic memory comprises spatiotemporal neural activity patterns.

20. The method of claim 12, wherein:
the pre-recorded neurostimulation data stored in the electronic memory is representative of patterns of stimulation of the subject's olfactory system including one or more of the subject's olfactory cortex, piriform cortex, and olfactory bulb, the pre-recorded neurostimulation data associated with one or more predetermined odors; and
the focused ultrasound transducer delivers transcranial stimulation to one or more of the subject's olfactory cortex, piriform cortex, and olfactory bulb to recreate a sense of one or more of the predetermined odors or variations of the one or more of the predetermined odors.

21. The method of claim 12, wherein:
the pre-recorded neurostimulation data stored in the electronic memory is representative of patterns of stimulation of one or more of the subject's vision, hearing, touch, and taste organs; and
the focused ultrasound transducer delivers transcranial stimulation to one or more of a vision, hearing, touch, and taste sense organ-processing region or regions of the subject's brain to recreate a sense of one or more of a vision, hearing, touch, and taste response.

* * * * *